(12) United States Patent
Dixon et al.

(10) Patent No.: US 6,287,865 B1
(45) Date of Patent: Sep. 11, 2001

(54) CF-2 PLANT PATHOGEN RESISTANCE GENES

(75) Inventors: Mark Stewart Dixon, Norwich (GB); David A. Jones, Canberra (AU); Jonathan Dallas George Jones, Norfolk (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/353,585

(22) Filed: Jul. 15, 1999

Related U.S. Application Data

(63) Continuation of application No. 08/930,277, filed on Oct. 27, 1997, now abandoned.

(30) Foreign Application Priority Data

Mar. 31, 1995 (GB) .................................................. 9506658

(51) Int. Cl.[7] .............................. C07H 21/04; C12N 5/14; C12N 1/21; C12N 15/63

(52) U.S. Cl. .................. 435/468; 435/252.3; 435/320.1; 435/71.1; 435/69.1; 435/471; 435/419; 435/440; 536/23.1; 536/23.6; 536/24.3

(58) Field of Search .............................. 435/6, 91.2, 468; 435/471, 410, 411, 419, 252.3, 320.1, 440; 536/23.6, 24.3, 24.33, 25.4, 23.1

(56) References Cited

U.S. PATENT DOCUMENTS 5,200,314 * 4/1993 Urdea ....................................... 435/6
5,728,820 * 3/1998 Akerblom ........................... 536/23.5

FOREIGN PATENT DOCUMENTS

WOA90 12097 10/1990 (WO) .
WOA93 07259 4/1993 (WO) .

(List continued on next page.)

OTHER PUBLICATIONS

Cell, vol. 84, Feb. 9, 1996 pp. 451–459, XP002007013 Dixon, M.S., et al: "The tomato cf–2 disease resistance locus comprises two functional genes encoding leucine–rich repeat proteins" cited in the application see whole document.

Journal of Cellular Biochmistry Supplement, vol. 21a, Mar. 10, 1995, p. 485 XP002007014 Dixon, M.S., et al.: "Cloning and characterisation of the cf–2 disease resistance gene, related family members and the corresponding null locus" see abstract J–203.

Molecular Plant_Microbe Interactions, vol. 6, 1993, pp. 348–357, XP000574564 Jones, D.A., et al.: "Two complex resistance loci revealed in tomato by classical and RFLP mapping of the cf–2, cf–4, cf–5 and cf–9 genes for resistance to *Cladosporium fulvum*" cited in the application see the whole document.

Trends in Genetics, vol. 11, No. 2, Feb. 1995, pp. 63–68, XP002006911 Tanksley, S.D., et al.: "Chromosomes landing: aparadigm for map–based gene cloning in plants with large genomes" see the whole document.

(List continued on next page.)

Primary Examiner—Carla J. Myers
(74) Attorney, Agent, or Firm—Nixon & Vanderhye P.C.

(57) ABSTRACT

The tomato Cf-2 gene has been cloned and its sequence provided, along with the encoded amino acid sequence. DNA encoding the polypeptide, and alleles, mutants and derivatives thereof, may be introduced into plant cells and the encoded polypeptide expressed, conferring pathogen resistance on plants comprising such cells and descendants thereof. The Cf-2 sequence comprises leucine rich repeats and the presence of such repeats enables identification of other plant pathogen resistance genes. Homologies to Cf-9 reveal motifs useful in the identification of other plant pathogen resistance genes.

8 Claims, 14 Drawing Sheets

FOREIGN PATENT DOCUMENTS

Figure 1:
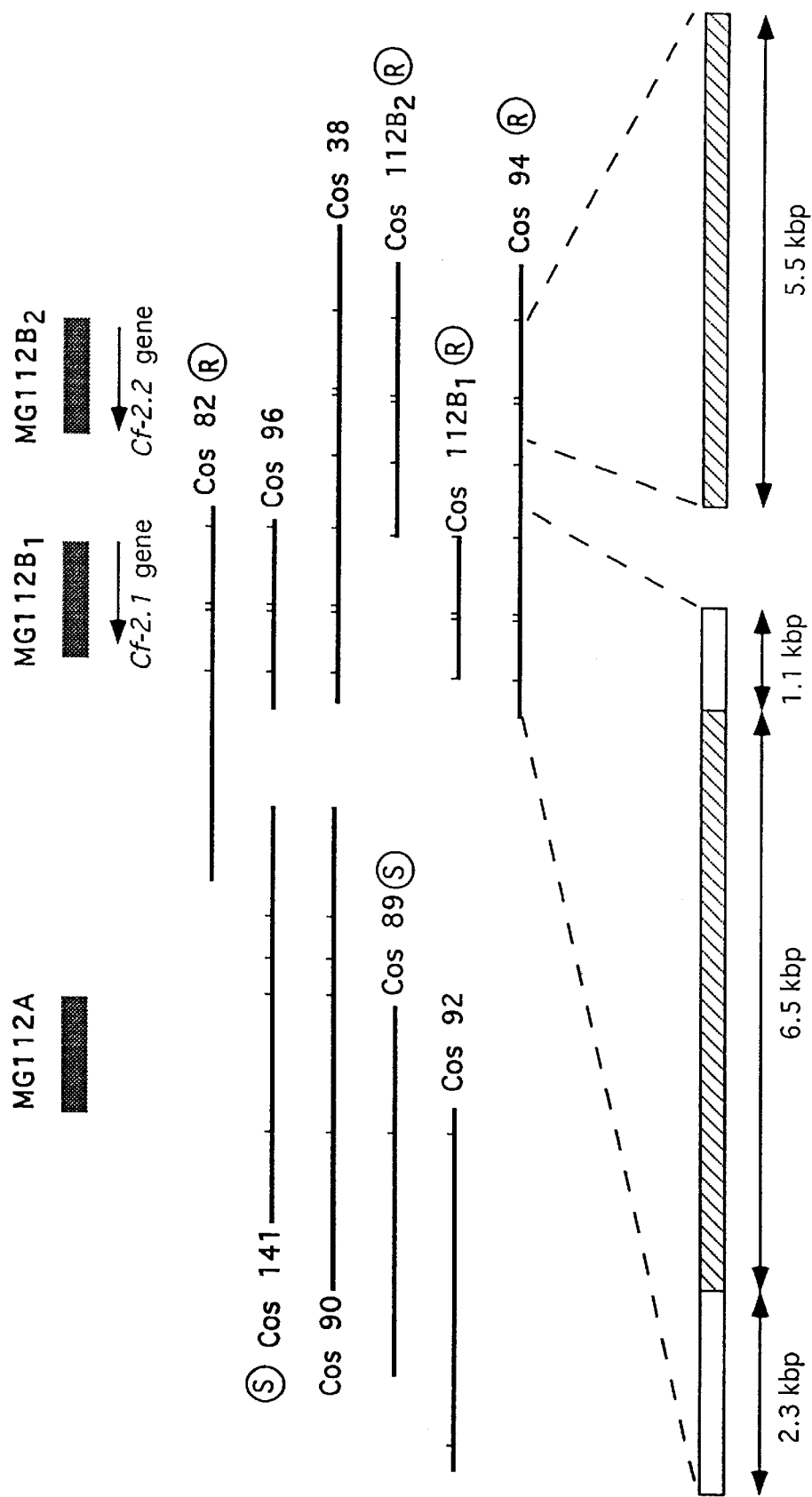

| | | |
|---|---|---|
| WOA93 16182 | 8/1993 | (WO) . |
| WOA93 22454 | 11/1993 | (WO) . |
| WOA94 29486 | 12/1994 | (WO) . |
| WOA95 05731 | 3/1995 | (WO) . |
| WOA95 28423 | 10/1995 | (WO) . |
| WOA95 31564 | 11/1995 | (WO) . |

OTHER PUBLICATIONS

Current Plant Science and Biotechnology in Agriculture, vol. 10, 1991, pp. 276–279, XP002007015 Dickinson, M., et al.: "Strategies for the cloning of genes in tomato for resistance to *Fulvia Fulva*" see the whole document.

Molecular Plant–Microbe Interactions, vol. 6, 1993, pp. 341–347, XP000574563 Dickinson, M., et al.: Close linkage between the cf–2/cf–5 and Mi resistance loci in tomato: cited in the application see the whole document.

Molecular Plant–Microbe Interactions, vol. 8, 1995, pp. 200–206, XP000574565 Dixon, M.S., et al.: "High resolution mapping of physical location of the tomato cf–2 gene" cited in the application see the whole document.

Plant Physiology, vol. 101, 1993, pp. 709,–712, XP002006913 Cornelissen, B.J.C., et al.: "Strategies for control of fungal diseases with transgenic plants" see p. 709, lest–hand column, last paragraph—p. 710, left–hand column, line 1.

Cell vol. 80, Feb. 10, 1995, pp. 363–366, XP002006912 Dangl, J.L.: "Piece de Resistance: novel classes of plant disease resistance genes" see p. 363, left–hand column, last line—right–hand column.

Jones et al, "Isolation of the Tomato Cf–9 Gene for Resistance to *Cladosporium fulvum* by Transposon Tagging", Science 266:789–793 (1994).

* cited by examiner

FIGURE 2A

```
   1  CTCGAGTTCG GAACCTAAAA GGTATAAAAT ATTAATAAAA ATTTTAAAAT
  51  GGTATATCAA TTTTTATATT AACCAAAACG TCAAAATCGC TGAAACAACA
 101  GCGATTTCCT TCACCGGAAA AAGCAAAATC GCTACTACTG CAGCGATTTT
 151  GCAAAATGTA ACTTTTTTTT AAAAAAATGC ATATTTCTT  ATAAGCTATA
 201  TATTTGAATT TCAAAAAAAA TATTTGAAAA TCAATAAAAT TTGTTTTTCC
 251  TACGATTTTC TTTTTAAAAT TCTTTTTTTG GAAAATCCCT ACCTAGGCAG
 301  CGATTTCCAT TTTTAATTTT TTTTAAATAA AAGGCAGCGA TTTTCGAAAA
 351  AAAAAATTTT AAAAAAAATT GAAAAGTCG  CTGCCTAGGT AGCGATTTGA
 401  ATTTTTTTAA AAAATGTTAT ATTTTGCAAA ATCGTTGCAG TAGCAACGAT
 451  TTTGCTTTTT TTGGAGGAAA TCGCTGTTGT TCCAGCGATT TTGCCGTTTT
 501  GGTTAATATA AAATTTTATA TAACGTTTTG AAATTTTTGT TAATATTTTA
 551  TAACTTTTAG GCTCCGGACT CAAGATTACT CCCTCTATCT TAGTTTATAA
 601  TGCATAGTCT GAATTTTGAA GAGCCAAATA GTTTAATTTT CGCCATAAAT
 651  TCAGACATGA AATCTTTAAA AAAGTTTAAA TAAAATTTGT ATATGTTGAA
 701  ACTACAGAAA AAGTATTATA ATTCACGATA ATTTATTCAC AAGCCATCGT
 751  CGGAGTGATC GCGAGTGAAG TGAAAGAATT GGAGTTTTTG ATATCCAGAA
 801  TCCATCTTGA GAGGTTGAGA TATCTTAATC TATCTCCAAT AAAAAAAAAC
 851  TATTAATATC CAATTTTCTT GAAGGCCATT ACCTATTCCG ACAAATTCCA
 901  CAAGATACTT CATCATATAA AAAAATAATC TCCGTGAAGA AATTCTTTTA
 951  TTTGGAAAAT CGATTTTAGA GTCATTGCAA TTTAATTTTA TCAAATATT
1001  TGAGCATGAA AAATTTGAAA TGGAGGTGTC ATAAAAATAA AATACCCTTT
1051  AAAACACGGC TTTATTGAGT TGACGATAGT TCAAGTAGGG AAAATAAATA
1101  ACTTATTAAT TGAATATAAA ACTTGCAAGA AAAAGTGAT  ATTCAAATTT
1151  AATTCTGACC ATTATCTCTT GATATTCTTT GCTCTTCATT TATTTGAATA
1201  TTCATTTTTC AAAAGTTCCA CGTCATAAGA CATCAAATAT CAAGTAGGTC
1251  CCATAAAAAT AAAATACCCT TCTCAACATG ACAAGAAAG  ATTGAAAAAT
1301  GACTAACATT TTCTCAAAGA CAAAAACAAA ACATGTGAGA GAAGACATTA
1351  CGAATCATCA TAATCTCTGA GACTGAGAAT TGTTAGATAT GGTCCACTAC
1401  TGTAGAGATG AGAATTTTGA ACCAAATGTA TTATACACTA AGAGTGGTCA
1451  TGATCATTGT GTGATAACAA AACTATTTTG GCAACTTTGA CTCAGTCCTT
```

FIGURE 2B

```
1501 GGCTAAATTA GACCTCTAAC ACAAAACAAT CCAAAAGTTG ACTTGAGAAT
1551 GACAACATTT TCTTCCCTGA TAGCAACCAA ATTAGCAAAT TTGGAAAAAA
1601 CGCGTGTCTT GTTGATCTTT AATTAGTATA AGTTACGTAC AATATCCTAT
1651 TGAATTGGAA ACAATAAACT CAAACTATGA TGATGGTTTC TAGAAAAGTA
1701 GTCTCTTCAC TTCAGTTTTT CACTCTTTTC TACCTCTTTA CAGTTGCATT
1751 TGCTTCGACT GAGGAGGCAA CTGCCCTCTT GAAATGGAAA GCAACTTTCA
1801 AGAACCAGAA TAATTCCTTT TTGGCTTCAT GGATTCCAAG TTCTAATGCA
1851 TGCAAGGACT GGTATGGAGT TGTATGCTTT AATGGTAGGG TAAACACGTT
1901 GAATATTACA AATGCTAGTG TCATTGGTAC ACTCTATGCT TTTCCATTTT
1951 CATCCCTCCC TTCTCTTGAA AATCTTGATC TTAGCAAGAA CAATATCTAT
2001 GGTACCATTC CACCTGAGAT TGGTAATCTC ACAAATCTTG TCTATCTTGA
2051 CTTGAACAAC AATCAGATTT CAGGAACAAT ACCACCACAA ATCGGTTTAC
2101 TAGCCAAGCT TCAGATCATC CGCATATTTC ACAATCAATT AAATGGATTT
2151 ATTCCTAAAG AAATAGGTTA CCTAAGGTCT CTTACTAAGC TATCTTTGGG
2201 TATCAACTTT CTTAGTGGTT CCATTCCTGC TTCAGTGGGG AATCTGAACA
2251 ACTTGTCTTT TTTGTATCTT TACAATAATC AGCTTTCTGG CTCTATTCCT
2301 GAAGAAATAA GTTACCTAAG ATCTCTTACT GAGCTAGATT TGAGTGATAA
2351 TGCTCTTAAT GGCTCTATTC CTGCTTCATT GGGGAATATG AACAACTTGT
2401 CTTTTTTGTT TCTTTATGGA AATCAGCTTT CTGGCTCTAT TCCTGAAGAA
2451 ATATGTTACC TAAGATCTCT TACTTACCTA GATTTGAGTG AGAATGCTCT
2501 TAATGGCTCT ATTCCTGCTT CATTGGGGAA TTTGAACAAC TTGTCTTTTT
2551 TGTTTCTTTA TGGAAATCAG CTTTCTGGCT CTATTCCTGA AGAAATAGGT
2601 TACCTAAGAT CTCTTAATGT CCTAGGTTTG AGTGAGAATG CTCTTAATGG
2651 CTCTATTCCT GCTTCATTGG GAATCTGAA AAACTTGTCT AGGTTGAATC
2701 TTGTTAATAA TCAGCTTTCT GGCTCTATTC CTGCTTCATT GGGGAATCTG
2751 AACAACTTGT CTATGTTGTA TCTTTACAAT AACCAGCTTT CTGGCTCTAT
2801 TCCTGCTTCA TTGGGGAATC TGAACAACTT GTCTATGTTG TATCTTTACA
2851 ATAATCAGCT TTCTGGCTCT ATTCCTGCTT CATTGGGGAA TCTGAACAAC
2901 TTGTCTAGGT TGTATCTCTA CAATAATCAG CTTTCTGGCT CTATTCCTGA
2951 AGAAATAGGT TACTTGAGTT CTCTTACTTA TCTAGATTTG AGTAATAACT
```

FIGURE 2C

```
3001  CCATTAATGG ATTTATTCCT GCTTCATTTG GCAATATGAG CAACTTGGCT
3051  TTTTTGTTTC TTTATGAAAA TCAGCTTGCT AGCTCTGTTC CTGAAGAAAT
3101  AGGTTACCTA AGGTCTCTTA ATGTCCTTGA TTTGAGTGAG AATGCTCTTA
3151  ATGGCTCTAT TCCTGCTTCA TTCGGGAATT TGAACAACTT GTCTAGGTTG
3201  AATCTTGTTA ATAATCAGCT TTCTGGCTCT ATTCCTGAAG AAATAGGTTA
3251  CCTAAGGTCT CTTAATGTCC TTGATTTGAG TGAGAATGCT CTTAATGGCT
3301  CTATTCCTGC TTCATTCGGG AATTTGAACA ACTTGTCTAG GTTGAATCTT
3351  GTTAATAATC AGCTTTCTGG CTCTATTCCT GAAGAAATAG GTTACCTAAG
3401  ATCTCTTAAT GACCTAGGTT TGAGTGAGAA TGCTCTTAAT GGCTCTATTC
3451  CTGCTTCATT GGGGAATCTG AACAACTTGT CTATGTTGTA TCTTTACAAT
3501  AATCAGCTTT CTGGCTCTAT TCCTGAAGAA ATAGGTTACT TGAGTTCTCT
3551  TACTTATCTA TCTTTGGGTA ATAACTCTCT TAATGGACTT ATTCCTGCTT
3601  CATTTGGCAA TATGAGAAAT CTGCAAGCTC TGATTCTCAA TGATAACAAT
3651  CTCATTGGGG AAATTCCTTC ATCTGTGTGC AATTTGACAT CACTGGAAGT
3701  GTTGTATATG CCGAGAAACA ATTTGAAGGG AAAAGTTCCG CAATGTTTGG
3751  GTAATATCAG TAACCTTCAG GTTTTGTCGA TGTCATCTAA TAGTTTCAGT
3801  GGAGAGCTCC CTTCATCTAT TTCCAATTTA ACATCACTAC AAATACTTGA
3851  TTTTGGCAGA AACAATCTGG AGGGAGCAAT ACCACAATGT TTTGGCAATA
3901  TTAGTAGCCT CGAGGTTTTT GATATGCAGA ACAACAAACT TTCTGGGACT
3951  CTTCCAACAA ATTTTAGCAT TGGATGTTCA CTGATAAGTC TCAACTTGCA
4001  TGGCAATGAA CTAGAGGATG AAATCCCTCG GTCTTTGGAC AATTGCAAAA
4051  AGCTGCAAGT TCTTGATTTA GGAGACAATC AACTCAACGA CACATTTCCC
4101  ATGTGGTTGG GAACTTTGCC AGAGCTGAGA GTTTTAAGGT TGACATCGAA
4151  TAAATTGCAT GGACCTATAA GATCATCAAG GGCTGAAATC ATGTTTCCTG
4201  ATCTTCGAAT CATAGATCTC TCTCGCAATG CATTCTCGCA AGACTTACCA
4251  ACGAGTCTAT TTGAACATTT GAAAGGGATG AGGACAGTTG ATAAAACAAT
4301  GGAGGAACCA AGTTATGAAA GCTATTACGA TGACTCGGTG GTAGTTGTGA
4351  CAAAGGGATT GGAGCTTGAA ATTGTGAGAA TTTTGTCTTT GTACACAGTT
4401  ATCGATCTTT CAAGCAACAA ATTTGAAGGA CATATTCCTT CTGTCCTGGG
4451  AGATCTCATT GCGATCCGTA TACTTAATGT ATCTCATAAT GCATTGCAAG
```

FIGURE 2D

```
4501  GCTATATACC ATCATCACTT GGAAGTTTAT CTATACTGGA ATCACTAGAC
4551  CTTTCGTTTA ACCAACTTTC AGGAGAGATA CCACAACAAC TTGCTTCTCT
4601  TACGTTTCTT GAATTCTTAA ATCTCTCCCA CAATTATCTC CAAGGATGCA
4651  TCCCTCAAGG ACCTCAATTC CGTACCTTTG AGAGCAATTC ATATGAAGGT
4701  AATGATGGAT TACGTGGATA TCCAGTTTCA AAAGGTTGTG GCAAAGATCC
4751  TGTGTCAGAG AAAAACTATA CAGTGTCTGC GCTAGAAGAT CAAGAAAGCA
4801  ATTCTGAATT TTTCAATGAT TTTTGGAAAG CAGCTCTGAT GGGCTATGGA
4851  AGTGGACTGT GTATTGGCAT ATCCATGATA TATATCTTGA TCTCGACTGG
4901  AAATCTAAGA TGGCTTGCAA GAATCATTGA AAAACTGGAA CACAAAATTA
4951  TCATGCAAAG GAGAAGAAG CAGCGAGGTC AAAGAAATTA CAGAAGAAGA
5001  AATAATCACT TCTAGACAAG TTACCAATAC AGAAAGATTT GATTTCAGAA
5051  CTTCAGGTAT TCACGCTAAG CTCTAACACT TATCTTTTTT AGTTTATTCT
5101  AACAACTAAT ATATGGTTTT TTTTATCAA CAAATACTTA TTAAGGCTTG
5151  ATACAAATTG CTATAATCAC TTGGAAGCTG TGATATATAA CAAAGCCTAA
5201  AAATTTATAG TTGTGTGACT CACTTTCTTA TTTTTCAGAT TTTCAGGAGC
5251  CAAGAATTAG AAGACGCTGG TGTAAAGGAT TTGCTTCTTC CTATGTTGCA
5301  GCTTATGATT GTTGGATTTG ATTTTTAGTT TTATAAGGTT TTCTTCAGTT
5351  GGGAAAATGT AATATTTTGA ATTTTGATGA TATATAATAA ATGTTGTGTA
5401  TTGAATGATG TGTATGCATT TCTCGGATCA ATAATACTCA CCTCAAAGAA
5451  TCTAAGAGAG TTAGCGCACG ATAGAAGATA GAACATACAA AGAAGAATAC
5501  ATTACAACCT TGGGCTTGGT TATCTTACAC CCCAAAGCTT GTTATTATGG
5551  AAGGAAAGGC CAAGTTTTAT TTTTAGATAT GGGGAGCCTT GGCGTGCTGG
5601  TAAGGTTGTA GTGGATAAGG TAACTTCTCC TGTTAATGAA TTGAATGATC
5651  ATAGCAGAGA TGTGTTTAAA ATTTCTGTTG TATTAGTTTG TAATATTTGG
5701  AGGTCTTAAA TTGAACAGAT GCACATCTGT TCGTGAAAGA GCATGACTAT
5751  TCTTATAAGT CAACTCTCAA GTTCTATAAA TATAAGGACT CCTAAAGTAG
5801  CATAAGAAAA AACTGCAGTA TACTAAGGCG TTGTTGGATC CTGAAGGGAA
5851  TTGCTGGTAA CCCCCTAAAC AACATACGTT ATATTGGTGG GGGGTAGAAG
5901  GTACCCAGTG AAATAATCTA GGTTTGCATA GGTTGCTCTG CAAACAACAA
5951  TTATTAAACA AAATCCACAC ACACTAGCAC ATGAGAGTAA AAAATTTAAT
```

FIGURE 2E

```
6001  GACGAGATGA AAGAAACTCA CGCCAAGATG GACTTTATCA AACAACAAAT
6051  ACATTGTTTG TACCTTTTGG ACAACCATTT ATCACTCAAA GAAGATCAAG
6101  GATTGATGCA TTACATCGTT CTTGGAACAA AATTATGTAC ATAAAACTTA
6151  CAGGAATCAT GTTTTGTGTG TGGTAAAACT CCATAAGGAC TAGTCCAAGA
6201  TACTGAGATC AAGGATTTCT AAGTGCAGCC AATCTCTTCT CCAGTTCATC
6251  GATCCCCGAA CTGCCAGCAC GAAAGCACAA CAACAAAATG TACATGAGCG
6301  AGTTACTGAG ATCAAAGAGC ATGAAAAAAG GCACTTCATA CTAATATGAT
6351  AACTTCATAC TAATATGATA CAATTATTTA CAGGAAGAAA AGAAGAATAG
6401  GAAACCGAAC CGCAACATAC TTTATCTATT AACGAGCAGT GCACTCAAGA
6451  TAACTAGTAT TTTTGCTCGA G
```

FIGURE 3A

```
   1  MMMVSRKVVS  SLQFFTLFYL  FTVAFASTEE  ATALLKWKAT  FKNQNNSFLA
  51  SWIPSSNACK  DWYGVVCFNG  RVNTLNITNA  SVIGTLYAFP  FSSLPSLENL
 101  DLSKNNIYGT  IPPEIGNLTN  LVYLDLNNNQ  ISGTIPPQIG  LLAKLQIIRI
 151  FHNQLNGFIP  KEIGYLRSLT  KLSLGINFLS  GSIPASVGNL  NNLSFLYLYN
 201  NQLSGSIPEE  ISYLRSLTEL  DLSDNALNGS  IPASLGNMNN  LSFLFLYGNQ
 251  LSGSIPEEIC  YLRSLTYLDL  SENALNGSIP  ASLGNLNNLS  FLFLYGNQLS
 301  GSIPEEIGYL  RSLNVLGLSE  NALNGSIPAS  LGNLKNLSRL  NLVNNQLSGS
 351  IPASLGNLNN  LSMLYLYNNQ  LSGSIPASLG  NLNNLSMLYL  YNNQLSGSIP
 401  ASLGNLNNLS  RLYLYNNQLS  GSIPEEIGYL  SSLTYLDLSN  NSINGFIPAS
 451  FGNMSNLAFL  FLYENQLASS  VPEEIGYLRS  LNVLDLSENA  LNGSIPASFG
 501  NLNNLSRLNL  VNNQLSGSIP  EEIGYLRSLN  VLDLSENALN  GSIPASFGNL
 551  NNLSRLNLVN  NQLSGSIPEE  IGYLRSLNDL  GLSENALNGS  IPASLGNLNN
 601  LSMLYLYNNQ  LSGSIPEEIG  YLSSLTYLSL  GNNSLNGLIP  ASFANMRNLQ
 651  ALILNDNNLI  GEIPSSVCNL  TSLEVLYMPR  NNLKGKVPQC  LGNISNLQVL
 701  SMSSNSFSGE  LPSSISNLTS  LQILDFGRNN  LEGAIPQCFG  NISSLEVFDM
 751  QNNKLSGTLP  TNFSIGCSLI  SLNLHGNELE  DEIPRSLDNC  KKLQVLDLGD
 801  NQLNDTFPMW  LGTLPELRVL  RLTSNKLHGP  IRSSRAEIMF  PDLRIIDLSR
 851  NAFSQDLPTS  LFEHLKGMRT  VDKTMEEPSY  ESYYDDSVVV  VTKGLELEIV
 901  RILSLYTVID  LSSNKFEGHI  PSVLGDLIAI  RILNVSHNAL   QGYIPSSLGS
 951  LSILESLDLS  FNQLSGEIPQ  QLASLTFLEF  LNLSHNYLQG  CIPQGPQFRT
1001  FESNSYEGND  GLRGYPVSKG  CGKDPVSEKN  YTVSALEDQE  SNSEFFNDFW
1051  KAALMGYGSG  LCIGISMIYI  LISTGNLRWL  ARIIEKLEHK  IIMQRRKKQR
1101  GQRNYRRRNN  HF*
```

FIGURE 3B

```
   1 MMMVSRKVVS SLQFFTLFYL FTVAFASTEE ATALLKWKAT FKNQNNSFLA
  51 SWIPSSNACK DWYGVVCFNG RVNTLNITNA SVIGTLYAFP FSSLPSLENL
 101 DLSKNNIYGT IPPEIGNLTN LVYLDLNNNQ ISGTIPPQIG LLAKLQIIRI
 151 FHNQLNGFIP KEIGYLRSLT KLSLGINFLS GSIPASVGNL NNLSFLYLYN
 201 NQLSGSIPEE ISYLRSLTEL DLSDNALNGS IPASLGNMNN LSFLFLYGNQ
 251 LSGSIPEEIC YLRSLTYLDL SENALNGSIP ASLGNLNNLS FLFLYGNQLS
 301 GSIPEEIGYL RSLNVLGLSE NALNGSIPAS LGNLKNLSRL NLVNNQLSGS
 351 IPASLGNLNN LSMLYLYNNQ LSGSIPASLG NLNNLSMLYL YNNQLSGSIP
 401 ASLGNLNNLS RLYLYNNQLS GSIPEEIGYL SSLTYLDLSN NSINGFIPAS
 451 FGNMSNLAFL FLYENQLASS VPEEIGYLRS LNVLDLSENA LNGSIPASFG
 501 NLNNLSRLNL VNNQLSGSIP EEIGYLRSLN VLDLSENALN GSIPASFGNL
 551 NNLSRLNLVN NQLSGSIPEE IGYLRSLNDL GLSENALNGS IPASLGNLNN
 601 LSMLYLYNNQ LSGSIPEEIG YLSSLTYLSL GNNSLNGLIP ASFANMRNLQ
 651 ALILNDNNLI GEIPSSVCNL TSLEVLYMPR NNLKGKVPQC LGNISNLQVL
 701 SMSSNSFSGE LPSSISNLTS LQILDFGRNN LEGAIPQCFG NISSLEVFDM
 751 QNNKLSGTLP TNFSIGCSLI SLNLHGNELE DEIPRSLDNC KKLQVLDLGD
 801 NQLNDTFPMW LGTLPELRVL RLTSNKLHGP IRSSRAEIMF PDLRIIDLSR
 851 NAFSQDLPTS LFEHLKGMRT VDKTMEEPSY ESYYDDSVVV VTKGLELEIV
 901 RILSLYTVID LSSNKFEGHI PSVLGDLIAI RILNVSHNAL  QGYIPSSLGS
 951 LSILESLDLS FNQLSGEIPQ QLASLTFLEF LNLSHNYLQG CIPQGPQFRT
1001 FESNSYEGND GLRGYPVSKG CGKDPVSEKN YTVSALEDQE SNSEFFNDFW
1051 KAALMGYGSG LCIGIS_I_IYI LISTGNLRWL ARI_EE_LEHK IIMQRRKKQR
1101 GQRNYRRRNN _RF_*
```

FIGURE 4A

```
   1  GGTTTCTAGA AAAGTAGTCT CTTCACTTCA GTTTTTCACT CTTTTCTACC
  51  TCTTTACAGT TGCATTTGCT TCGACTGAGG AGGCAACTGC CCTCTTGAAA
 101  TGGAAAGCAA CTTTCAAGAA CCAGAATAAT TCCTTTTTGG CTTCATGGAT
 151  TCCAAGTTCT AATGCATGCA AGGACTGGTA TGGAGTTGTA TGCTTTAATG
 201  GTAGGGTAAA CACGTTGAAT ATTACAAATG CTAGTGTCAT TGGTACACTC
 251  TATGCTTTTC CATTTTCATC CCTCCCTTCT CTTGAAAATC TTGATCTTAG
 301  CAAGAACAAT ATCTATGGTA CCATTCCACC TGAGATTGGT AATCTCACAA
 351  ATCTTGTCTA TCTTGACTTG AACAACAATC AGATTTCAGG AACAATACCA
 401  CCACAAATCG GTTACTAGC CAAGCTTCAG ATCATCCGCA TATTTCACAA
 451  TCAATTAAAT GGATTTATTC CTAAAGAAAT AGGTTACCTA AGGTCTCTTA
 501  CTAAGCTATC TTTGGGTATC AACTTTCTTA GTGGTTCCAT TCCTGCTTCA
 551  GTGGGGAATC TGAACAACTT GTCTTTTTTG TATCTTTACA ATAATCAGCT
 601  TTCTGGCTCT ATTCCTGAAG AAATAAGTTA CCTAAGATCT CTTACTGAGC
 651  TAGATTTGAG TGATAATGCT CTTAATGGCT CTATTCCTGC TTCATTGGGG
 701  AATATGAACA ACTTGTCTTT TTTGTTTCTT TATGGAAATC AGCTTTCTGG
 751  CTCTATTCCT GAAGAAATAT GTTACCTAAG ATCTCTTACT TACCTAGATT
 801  TGAGTGAGAA TGCTCTTAAT GGCTCTATTC CTGCTTCATT GGGGAATTTG
 851  AACAACTTGT CTTTTTTGTT TCTTTATGGA AATCAGCTTT CTGGCTCTAT
 901  TCCTGAAGAA ATAGGTTACC TAAGATCTCT TAATGTCCTA GGTTTGAGTG
 951  AGAATGCTCT TAATGGCTCT ATTCCTGCTT CATTGGGGAA TCTGAAAAAC
1001  TTGTCTAGGT TGAATCTTGT TAATAATCAG CTTTCTGGCT CTATTCCTGC
1051  TTCATTGGGG AATCTGAACA ACTTGTCTAT GTTGTATCTT ACAATAACC
1101  AGCTTTCTGG CTCTATTCCT GCTTCATTGG GGAATCTGAA CAACTTGTCT
1151  ATGTTGTATC TTTACAATAA TCAGCTTTCT GGCTCTATTC CTGCTTCATT
1201  GGGGAATCTG AACAACTTGT CTAGGTTGTA TCTCTACAAT AATCAGCTTT
1251  CTGGCTCTAT TCCTGAAGAA ATAGGTTACT GAGTTCTCT TACTTATCTA
1301  GATTTGAGTA ATAACTCCAT TAATGGATTT ATTCCTGCTT CATTTGGCAA
1351  TATGAGCAAC TTGGCTTTTT TGTTTCTTTA TGAAAATCAG CTTGCTAGCT
1401  CTGTTCCTGA AGAAATAGGT TACCTAAGGT CTCTTAATGT CCTTGATTTG
1451  AGTGAGAATG CTCTTAATGG CTCTATTCCT GCTTCATTCG GAATTTGAA
1501  CAACTTGTCT AGGTTGAATC TTGTTAATAA TCAGCTTTCT GGCTCTATTC
```

FIGURE 4B

```
1551  CTGAAGAAAT AGGTTACCTA AGGTCTCTTA ATGTCCTTGA TTTGAGTGAG
1601  AATGCTCTTA ATGGCTCTAT TCCTGCTTCA TTCGGGAATT TGAACAACTT
1651  GTCTAGGTTG AATCTTGTTA ATAATCAGCT TTCTGGCTCT ATTCCTGAAG
1701  AAATAGGTTA CCTAAGATCT CTTAATGACC TAGGTTTGAG TGAGAATGCT
1751  CTTAATGGCT CTATTCCTGC TTCATTGGGG AATCTGAACA ACTTGTCTAT
1801  GTTGTATCTT TACAATAATC AGCTTTCTGG CTCTATTCCT GAAGAAATAG
1851  GTTACTTGAG TTCTCTTACT TATCTATCTT TGGGTAATAA CTCTCTTAAT
1901  GGACTTATTC CTGCTTCATT TGGCAATATG AGAAATCTGC AAGCTCTGAT
1951  TCTCAATGAT AACAATCTCA TTGGGGAAAT TCCTTCATCT GTGTGCAATT
2001  TGACATCACT GGAAGTGTTG TATATGCCGA GAAACAATTT GAAGGGAAAA
2051  GTTCCGCAAT GTTTGGGTAA TATCAGTAAC CTTCAGGTTT TGTCGATGTC
2101  ATCTAATAGT TTCAGTGGAG AGCTCCCTTC ATCTATTTCC AATTTAACAT
2151  CACTACAAAT ACTTGATTTT GGCAGAAACA ATCTGGAGGG AGCAATACCA
2201  CAATGTTTTG GCAATATTAG TAGCCTCGAG GTTTTTGATA TGCAGAACAA
2251  CAAACTTTCT GGGACTCTTC AACAAATTT TAGCATTGGA TGTTCACTGA
2301  TAAGTCTCAA CTTGCATGGC AATGAACTAG AGGATGAAAT CCCTCGGTCT
2351  TTGGACAATT GCAAAAGCT GCAAGTTCTT GATTTAGGAG ACAATCAACT
2401  CAACGACACA TTTCCCATGT GGTTGGGAAC TTTGCCAGAG CTGAGAGTTT
2451  TAAGGTTGAC ATCGAATAAA TTGCATGGAC CTATAAGATC ATCAAGGGCT
2501  GAAATCATGT TTCCTGATCT TCGAATCATA GATCTCTCTC GCAATGCATT
2551  CTCGCAAGAC TTACCAACGA GTCTATTTGA ACATTTGAAA GGGATGAGGA
2601  CAGTTGATAA AACAATGGAG GAACCAAGTT ATGAAAGCTA TTACGATGAC
2651  TCGGTGGTAG TTGTGACAAA GGGATTGGAG CTTGAAATTG TGAGAATTTT
2701  GTCTTTGTAC ACAGTTATCG ATCTTTCAAG CAACAAATTT GAAGGACATA
2751  TTCCTTCTGT CCTGGGAGAT CTCATTGCGA TCCGTATACT TAATGTATCT
2801  CATAATGCAT TGCAAGGCTA TACCATCA TCACTTGGAA GTTTATCTAT
2851  ACTGGAATCA CTAGACCTTT CGTTTAACCA ACTTTCAGGA GAGATACCAC
2901  AACAACTTGC TTCTCTTACG TTTCTTGAAT TCTTAAATCT CTCCCACAAT
2951  TATCTCCAAG GATGCATCCC TCAAGGACCT CAATTCCGTA CCTTTGAGAG
3001  CAATTCATAT GAAGGTAATG ATGGATTACG TGGATATCCA GTTTCAAAAG
3051  GTTGTGGCAA AGATCCTGTG TCAGAGAAAA ACTATACAGT GTCTGCGCTA
```

FIGURE 4C

```
3101  GAAGATCAAG AAAGCAATTC TGAATTTTTC AATGATTTTT GGAAAGCAGC
3151  TCTGATGGGC TATGGAAGTG GACTGTGTAT TGGCATATCC ATAATATATA
3201  TCTTGATCTC GACTGGAAAT CTAAGATGGC TTGCAAGAAT CATTGAAGAA
3251  CTGGAACACA AAATTATCAT GCAAGGAGA AAGAAGCAGC GAGGTCAAAG
3301  AAATTACAGA AGAAGAAATA ATCGCTTCTA GACAAGTTAC CAATACCGAA
3351  AGATTTGATT TCAGAACTTC AGACTTTCAG GAGCCAAGAA TAAGAAGACG
3401  CTGGTGTAAA GGATTTGCTT CTTCCTGTGT TGCAGCTTAT GATGTTGGAT
3451  TAGATTTTTA GTTTTATAAG CTTTTCTTCA GTTGGGAAAA TGTAATATTA
3501  TGAATTTGAT GATATACAAT AAATGTTGTG TTTATTGAAA AAAAAAAAA
3551  AAAAAAAAAA AAAAAAAAA AAA
```

FIGURE 5

| | | |
|---|---|---|
| Cf-2 | LGTLPELRVLRLTSNKLHGPIRSS    RAEI | 838 |
| Cf-9 | TNLFMGLQILDLSSNGFSGNLPERI | 620 |
| | | |
| Cf-2 | MFPDLRIIDLSRNAFSQDLPTS | 860 |
| Cf-9 | LGNLQTMKEIDES-TGFPEYISDPY | 644 |
| | | |
| Cf-2 | LFEHLKGMRTVDKTMEEPSYESYYDDSVVVVTKGLELEI | 899 |
| Cf-9 | DIYYNYLTTISTKGQD------YD-SVRI | 666 |
| | | |
| Cf-2 | VRILSLYTVIDLSSNKFEGHIPSV | 923 |
| Cf-9 | LDSNMIINLSKNRFEGHIPSI | 687 |
| | | |
| Cf-2 | LGDLIAIRILNVSHNALQGYIPSS | 947 |
| Cf-9 | IGDLVGLRTLNLSHNVLEGHIPAS | 711 |
| | | |
| Cf-2 | LGSLSILESLDLSFNQLSGEIPQQ | 971 |
| Cf-9 | FQNLSVLESLDLSSNKISGEIPQQ | 735 |
| | | |
| Cf-2 | LASLTFLEFLNLSHNYLQGCIPQG | 995 |
| Cf-9 | LASLTFLEVLNLSHNHLVGCIPKG | 759 |
| | | |
| Cf-2 | PQFRTFESNSYEGNDGLRGYPVSKGCGKDPVSEKNYTVSAL | 1036 |
| Cf-9 | KQFDSFGNTSYQGNDGLRGFPLSKLCGGDDQVTTPA | |
| | | |
| Cf-2 | E-DQESNSEFFNDFWK | 1051 |
| Cf-9 | ELDQEEEEED | 805 |
| | | |
| Cf-2 | AALMGYGSGLCIGISMIYILISTG | 1075 |
| Cf-9 | SPMISWQGVLVGYGCGLVIGLSVIYIMWSTQ | 842 |
| | | |
| Cf-2 | NLRWLARIIEKLEHKIIMQRRKKQRGQRNYRRRNNHF* | 1112 |
| Cf-9 | YPAWFSRMDLKLEHIITTKMKKHKKRY* | 863 |

FIGURE 6

```
Cf-2    LDLSFNQLSGEIPQQLASLTFLE-20aa-TFESNSYEGNDGLRGYPVSKGCG
Cf-9         S KI                      S GNT Q      F L  L
```

PEP SEQ1                              Ser-Gly-Glu-Ile-Pro-Gln-Gln

OLIGO 1 20mer                         768 fold degenerate

```
        (5') TCX-GGX-GAA-ATT-CCX-CAA-CA (3')
              G   C           G
                  A
```

PEP SEQ2                              Tyr-Glu-Gly-Asn-Asp-Gly-Leu-
Arg
                     Gln
```
        (5') TAT-GAA-GGX-AAT-GAT-GGX-CTX-CG (3')
              C C G           C   C
```

OLIGO 2 23mer                         2048 fold degenerate (Reverse)
```
        (5') CG-XAG-XCC-ATC-ATT-XCC-TTC-ATA (3')
                G   G           C G G
```

FIGURE 7

| | | |
|---|---|---|
| MMMVSRKVVSSLQFFTLFYLFTVAFA | 26 | A |
| STEEATALLKWKATFKNQNNSFLASWIPSSNACKDWY | 63 | B |
| GVVCFNGRVNTLNITNASVIGTLYA | 88 | |
| FPFSSLPSLENLDLSKNNIYGTIP | 112 | C |
| PEIGNLTNLVYLDLNNNQISGTIP | 136 | |
| PQIGLLAKLQIIRIFHNQLNGFIP | 160 | |
| KEIGYLRSLTKLSLGINFLSGSIP | 184 | |
| ASVGNLNNLSFLYLYNNQLSGSIP | 208 | |
| EEISYLRSLTELDLSDNALNGSIP | 232 | |
| ASLGNMNNLSFLFLYGNQLSGSIP | 256 | |
| EEICYLRSLTYLDLSENALNGSIP | 280 | |
| ASLGNLNNLSFLFLYGNQLSGSIP | 304 | |
| EEIGYLRSLNVLGLSENALNGSIP | 328 | |
| ASLGNLKNLSRLNLVNNQLSGSIP | 352 | |
| ASLGNLNNLSMLYLYNNQLSGSIP | 376 | |
| ASLGNLNNLSMLYLYNNQLSGSIP | 400 | |
| ASLGNLNNLSRLYLYNNQLSGSIP | 424 | |
| EEIGYLSSLTYLDLSNNSINGFIP | 448 | |
| ASFGNMSNLAFLFLYENQLASSVP | 472 | |
| EEIGYLRSLNVLDLSENALNGSIP | 496 | |
| ASFGNLNNLSRLNLVNNQLSGSIP | 520 | |
| EEIGYLRSLNVLDLSENALNGSIP | 544 | |
| ASFGNLNNLSRLNLVNNQLSGSIP | 568 | |
| EEIGYLRSLNDLGLSENALNGSIP | 592 | |
| ASLGNLNNLSMLYLYNNQLSGSIP | 616 | |
| EEIGYLSSLTYLSLGNNSLNGLIP | 640 | |
| ASFGNMRNLQALILNDNNLIGEIP | 664 | |
| SSLCNLTSLEVLYMPRNNLKGKVP | 698 | |
| QCLGNISNLQVLSMSSNSFSGELP | 712 | |
| SSISNLTSLQILDFGRNNLEGAIP | 736 | |
| QCFGNISSLEVFDMQNNKLSGTLP | 760 | |
| TNFSIGCSLISLNLHGNELEDEIP | 784 | |
| RSLDNCKKLQVLDLGDNQLNDTFP | 808 | |
| MWLGTLPELRVLRLTSNKLHGPIRSS | 834 | |
| RAEIMFPDLRIIDLSRNAFSQDLPT | 859 | |
| SLFEHLKGMRTVDKTMEEPSYESYYDDSVVVVTKGLEL | 897 | |
| EIVRILSLYTVIDLSSNKFEGHIP | 921 | |
| SVLGDLIAIRILNVSHNALQGYIP | 945 | |
| SSLGSLSILESLDLSFNQLSGEIP | 969 | |
| QQLASLTFLEFLNLSHNYLQGCIP | 993 | |
| QGPQFRTFESNSYEGNDGLRGYPVSKGCGK | 1023 | D |
| DPVSEKNYTVSALEDQESNSEFFNDFWK | 1051 | E |
| AALMGYGSGLCIGISMIYILISTG | 1075 | F |
| NLRWLARIIEKLEHKIIMQRRKKQRGQRNYRRRNNHF | 1112 | G |

CF-2 PLANT PATHOGEN RESISTANCE GENES

This application is a continuation of application Ser. No. 08/930,277, filed Oct. 27, 1997 now abandoned; which is a 371 of PCT/GB96/00785, filed Apr. 1, 1996.

The present invention relates to pathogen resistance in plants and more particularly the identification and use of pathogen resistance genes. It is based on cloning of the tomato Cf-2 gene.

Plants are constantly challenged by potentially pathogenic microorganisms. Crop plants are particularly vulnerable, because they are usually grown as genetically uniform monocultures; when disease strikes, losses can be severe. However, most plants are resistant to most plant pathogens. To defend themselves, plants have evolved an array of both preexisting and inducible defences. Pathogens must specialize to circumvent the defence mechanisms of the host, especially those biotrophic pathogens that derive their nutrition from an intimate association with living plant cells. If the pathogen can cause disease, the interaction is said to be compatible, but if the plant is resistant, the interaction is said to be incompatible. Race specific resistance is strongly correlated with the hypersensitive response (HR), an induced response by which (it is hypothesized) the plant deprives the pathogen of living host cells by localized cell death at sites of attempted pathogen ingress.

It has long been known that HR-associated disease resistance is often (though not exclusively) specified by dominant genes (R genes). Flor showed that when pathogens mutate to overcome such R genes, these mutations are recessive. Flor concluded that for R genes to function, there must also be corresponding genes in the pathogen, denoted avirulence genes (Avr genes). To become virulent, pathogens must thus stop making a product that activates R gene-dependent defence mechanisms (Flor, 1971). A broadly accepted working hypothesis, often termed the elicitor/receptor model, is that R genes encode products that enable plants to detect the presence of pathogens, provided said pathogens carry the corresponding Avr gene (Gabriel and Rolfe, 1990). This recognition is then transduced into the activation of a defence response.

Some interactions exhibit different genetic properties. *Helminthosporium carbonum* races that express a toxin (Hc toxin) infect maize lines that lack the Hm1 resistance gene. Mutations to loss of Hc toxin expression are recessive, and correlated with loss of virulence, in contrast to gene-for-gene interactions in which mutations to virulence are recessive. A major accomplishment was reported in 1992, with the isolation by tagging of the Hm1 gene (Johal and Briggs, 1992). Plausible arguments have been made for how gene-for-gene interactions could evolve from toxin-dependent virulence. For example, plant genes whose products were the target of the toxin might mutate to confer even greater sensitivity to the toxin, leading to HR, and the conversion of a sensitivity gene to a resistance gene. However, this does not seem to be the mode of action of Hm1, whose gene product inactivates Hc toxin.

Pathogen avirulence genes are still poorly understood. Several bacterial Avr genes encode hydrophilic proteins with no homology to other classes of protein, while others carry repeating units whose number can be modified to change the range of plants on which they exhibit avirulence (Keen, 1992; Long and Staskawicz, 1993). Additional bacterial genes (hzp genes) are required for bacterial Avr genes to induce HR, and also for pathogenicity (Keen, 1992; Long and Staskawicz, 1993). It is not clear why pathogens make products that enable the plant to detect them. It is widely believed that certain easily discarded Avr genes contribute to but are not required for pathogenicity, whereas other Avr genes are less dispensable (Keen, 1992; Long and Staskawicz, 1993). The characterization of one fungal avirulence gene has also been reported; the Avr9 gene of *Cladosporium fulvum*, which confers avirulence on *C. fulvum* races that attempt to attack tomato varieties that carry the Cf-9 gene, encodes a secreted cysteine-rich peptide with a final processed size of 28 amino acids but its role in compatible interactions is not clear (De Wit, 1992).

The technology for gene isolation based primarily on genetic criteria has improved dramatically in recent years, and many workers are currently attempting to clone a variety of R genes. Targets include (amongst others) rust resistance genes in maize, Antirrhinum and flax (by transposon tagging); downy mildew resistance genes in lettuce and Arabidopsis (by map based cloning and T-DNA tagging); *Cladosporium fulvum* (Cf) resistance genes in tomato (by tagging, map based cloning and affinity labelling with avirulence gene products); virus resistance genes in tomato and tobacco (by map based cloning and tagging); nematode resistance genes in tomato (by map based cloning); and genes for resistance to bacterial pathogens in Arabidopsis and tomato (by map based cloning).

The map based cloning of the tomato Pto gene that confers "gene-for-gene" resistance to the bacterial speck pathogen *Pseudomonas syringae* pv tomato (Pst) has been reported (Martin et al, 1993). A YAC (yeast artificial chromosome) clone was identified that carried restriction fragment length polymorphism (RFLP) markers that were very tightly linked to the gene. This YAC was used to isolate homologous cDNA clones. Two of these cDNAs were fused to a strong promoter, and after transformation of a disease sensitive tomato variety, one of these gene fusions was shown to confer resistance to Pst strains that carry the corresponding avirulence gene, AvrPto. These two cDNAs show homology to each other. Indeed, the Pto cDNA probe reveals a small gene family of at least six members, 5 of which can be found on the YAC from which Pto was isolated, and which thus comprise exactly the kind of local multigene family inferred from genetic analysis of other R gene loci.

The Pto gene CDNA sequence is puzzling for proponents of the simple elicitor/receptor model. It reveals unambiguous homology to serine/threonine kinases, consistent with a role in signal transduction Intriguingly, there is strong homology to the kinases associated with self incompatibility in Brassicas, which carry out an analogous role, in that they are required to prevent the growth of genotypically defined incompatible pollen tubes. However, in contrast to the Brassica SRK kinase (Stein et al 1991), the Pto gene appears to code for little more than the kinase catalytic domain and a potential N-terminal-myristoylation site that could promote association with membranes. It would be surprising if such a gene product could act alone to accomplish the specific recognition required to initiate the defence response only when the AvrPto gene is detected in invading microrganisms. The race-specific elicitor molecule made by Pst strains that carry AvrPto is still unknown and needs to be characterized before possible recognition of this molecule by the Pto gene product can be investigated.

Since the isolation of the Pto gene a number of other resistance genes have been isolated. The isolation of the tobacco mosaic resistance gene N from tobacco was reported by Whitham et al (1994). The isolation of the *Arabidopsis thaliana* gene for resistance to *Pseudomonas*

*syringae* RPS2 was reported by Bent et al (1994) and by Mindrinos et al (1994). These genes probably encode cytoplasmic proteins that carry a P-loop and a leucine-rich repeat. The ligands with which they interact are uncharacterised and it is not known what other plant proteins they interact with to accomplish the defence response. Our own laboratory has reported the isolation of the tomato Cf-9 which confers resistance against the fungus *Cladosporium fulvum*. This is a subject of a previous patent application (PCT/GB94/02812 published as WO 95/18230) and has been reported in Jones et al (1994). Cf-9 and Avr9 sequences, and sequences of the encoded polypeptides are given in WO95/18320 and Jones et al (1994).

We have now cloned Cf-2 genes.

WO93/11241 reports the sequence of a gene encoding a polygalacturonase inhibitor protein (PGIP) that has some homology with Cf-9 and, as we have now discovered, Cf-2 (the subject of the present invention). Cf-9, Cf-2 and others (Cf-4, 5 etc.) are termed by those skilled in the art "pathogen resistance genes" or "disease resistance genes". PGIP-encoding genes are not pathogen resistance genes. A pathogen resistance gene (R) enables a plant to detect the presence of a pathogen expressing a corresponding avirulence gene (Avr). When the pathogen is detected, a defence response such as the hypersensitive response (HR) is activated. By such means a plant may deprive the pathogen of living cells by localised cell death at sites of attempted pathogen ingress. On the other hand, the PGIP gene of WO93/11241 (for example) is a gene of the kind that is induced in the plant defence response resulting from detection of a pathogen by an R gene.

Thus, a pathogen resistance gene may be envisaged as encoding a receptor to a pathogen-derived and Avr dependent molecule. In this way it may be likened to the RADAR of a plant for detection of a pathogen, whereas PGIP is involved in the defence the plant mounts to the pathogen once detected and is not a pathogen resistance gene. Expression of a pathogen resistance gene in a plant causes activation of a defence response in the plant. This may be upon contact of the plant with a pathogen or a corresponding elicitor molecule, though the possibility of causing activation by over-expression of the resistance gene in the absence of elicitor has been reported. The defence response may be activated locally, e.g. at a site of contact of the plant with pathogen or elicitor molecule, or systemically. Activation of a defence response in a plant expressing a pathogen resistance gene may be caused upon contact of the plant with an appropriate, corresponding elicitor molecule, e.g. as produced by a *Cladosporium fulvum* avr gene as discussed. The elicitor may be contained in an extract of a pathogen such as *Cladosporium fulvum*, or may be wholly or partially purified and may be wholly or partially synthetic. An elicitor molecule may be said to "correspond" if it is a suitable ligand for the R gene product to elicit activation of a defence response.

The "Cf-x"/"Avrx" terminology is standard in the art. The Cf resistance genes and corresponding fungal avirulence genes (Avr) were originally defined genetically as interacting pairs of genes whose measurable activities fall into mutually exclusive interacting pairs. Avr9 elicits a necrotic response on Cf-9 containing tomatoes but no response on Cf-2 containing tomatoes, the moeity recognised by Cf-2 being different from that recognised by Cf-9.

Expression of Cf-2 function in a plant may be determined by investigating compatibility of various *C. fulvum* races.

A race of *C. fulvum* that carries functional copies of all known Avr genes (race 0) will grow (compatible) only on a tomato which lacks all the Cf genes. It will not grow (incompatible) on a plant carrying any functional Cf gene. If the *C. fulvum* race lacks a functional Avr2 gene (race 2) it will be able to grow not only on a plant lacking any Cf genes but also a plant carrying the Cf-2 gene. A race also lacking a functional Avr4 gene (race 2,4) will also be able to grow on a plant carrying the Cf-4 gene. A race only lacking a functional Avr4 gene (race 4) will not be able to grow on a plant carrying Cf-2. Similarly, a *C. fulvum* race 5 (lacking a functional Avr5 gene) will not be able to grow on a plant carrying a Cf-2 gene. Neither a race 4 nor a race 2,4 will be able to grow on a plant carrying any of the other Cf genes. Various races are commonly available in the art, e.g. from the Research Institute for Plant Protection (IPO-DLO), PO Box 9060, 6700 GW Wageningen, The Netherlands. A race 4 is available under accession number IPO10379 and a race 2,4 available under Accession number IPO50379.

We have now isolated two almost identical tomato genes, Cf-2.1 and Cf-2.2, which confer resistance against the fungus *Cladosporium fulvum* and we have sequenced the DNA and deduced the amino acid sequence from these genes. (Both genes are almost identical and any statement made herein about one should be considered as applying to both, unless context demands otherwise.) The DNA sequence of the tomato Cf-2.1 genomic gene is shown in FIG. 2 (SEQ ID NO. 1) and the deduced amino acid sequences (for both genes) are shown in FIGS. 3A and B (SEQ ID NO's 2 and 3).

As described in more detail below, the tomato Cf-2 genes were isolated by map-based cloning. In this technique the locus that confers resistance is mapped at high resolution relative to restriction fragment length polymorphism (RFLP) markers that are linked to the resistance gene. We identified a marker that appeared to be absolutely linked to the resistance gene and used probes corresponding to this marker to isolate binary vector cosmid clones from a stock that carried the Cf-2 gene locus. Two independent overlapping clones conferred disease resistance and the region of overlap contains a reading-frame which shows remarkable structural resemblance to the Cf-9 gene. Since this sequence is the primary constituent of the DNA that overlaps the two clones that complement, we are confident that this sequence must correspond to the Cf-2 gene. A second almost identical region on one of the cosmids was also able to confer disease resistance, indicating that there are two functional Cf-2 genes).

According to one aspect, the present invention provides a nucleic acid isolate encoding a pathogen resistance gene, the gene being characterized in that it comprises nucleic acid encoding the amino acid sequence shown in SEQ ID NO 2 or SEQ ID NO. 3 or a fragment thereof. The nucleic acid isolate may comprise DNA, and may comprise the sequence shown in SEQ ID NO 1 or a sufficient part to encode the desired polypeptide (eg. from the initiating methionine codon to the first in frame downstream stop codon). In one embodiment the DNA comprises a sequence of nucleotides which are the nucleotides 1677 to 5012 of SEQ ID NO 1, or a mutant, derivative or allele thereof. A further aspect of the invention provides a nucleic acid isolate encoding a pathogen resistance gene, or a fragment thereof, obtainable by screening a nucleic acid library with a probe comprising nucleotides 1677 to 5012 of SEQ ID NO 1, or a fragment, derivative, mutant or allele thereof, and isolating DNA which encodes a polypeptide able to confer pathogen resistance to a plant, such as resistance to *Cladosporium fulvum* (eg. expressing Avr2). The plant may be tomato. Suitable techniques are well known in the art.

Nucleic acid according to the present invention may encode the amino acid sequence shown in SEQ ID NO 2 or a mutant, derivative or allele of the sequence provided e.g. SEQ ID NO 3. Preferred mutants, derivatives and alleles are those which retain a functional characteristic of the protein encoded by the wild-type gene, especially the ability to confer pathogen resistance and most especially the ability to confer resistance against a pathogen expressing the Avr2 elicitor molecule. Changes to a sequence, to produce a mutant or derivative, may be by one or more of addition, insertion, deletion or substitution of one or more nucleotides in the nucleic acid, leading to the addition, insertion, deletion or subsitution of one or more amino acids. Of course, changes to the nucleic acid which make no difference to the encoded amino acid sequence are included.

Preferred embodiments of nucleic acid encoding the amino acid sequences shown in FIG. 3 (SEQ ID NO.'s 2 and 3) include encoding sequences shown in FIGS. 2 (SEQ ID NO: 1) and 4 (SEQ ID NO: 4), respectively. To encode amino acid SEQ ID NO. 3 (FIG. 3b), DNA may comprise a nucleotide sequence shown in FIG. 4 (SEQ ID NO. 5).

Also provided by an aspect of the present invention is nucleic acid comprising a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a polypeptide able to confer pathogen resistance on a host, i.e., includes a pathogen resistance gene. Preferred conditions for hybridisation are familiar to those skilled in the art, but are generally stringent enough for there to be positive hybridisation between the sequences of interest to the exlucsion of other sequences.

Although the polypeptides encoded by the Cf-2 and Cf-9 genes share a high degree of homology, the genes themselves are not sufficiently homologous to identify each other in genomic Southern blotting using a stringency of 2×SSC at 60° C. In a BLASTN search, the highest level of identity between the DNA sequences of Cf-2 and Cf-9 is 69% over a 428 base region.

Nucleic acid according to the present invention, for instance mutants, derivatives and alleles of the specific sequences disclosed herein, may be distinguished from Cf-9 by one or more of the following:

not being sufficiently homologous with Cf-9 for the nucleic acid of the invention and Cf-9 to identify each other in Southern blotting using a stringency of 2×SSC at 60° C.;

having greater than 70%, preferably greater than about 75%, greater than about 80%, greater than about 90% or greater than about 95% homology with the encoding sequence shown in FIG. 2 as nucleotides 1677–5012;

eliciting &defence response, in a plant expressing the nucleic acid, upon contact of the plant with Avr2 elicitor molecule, e.g. as provided by a *Cladosporium fulvum* race expressing Avr2;

eliciting a defence response, in a plant expressing the nucleic acid, upon contact of the plant with the *C. fulvum* race 4 deposited at and available from the Research Institute for Plant Protection (IPO-DLO), PO Box 9060, 6700 GW Wageningen, The Netherlands, under accession number IPO10379, or an extract thereof, but not eliciting a defence response in the plant upon its contact with the C. fulvum race 2,4 deposited at and available from the same institute under Accession number IPO50379, or an extract thereof;

not eliciting a defence response, in a plant expressing the nucleic acid, upon contact of the plant with Avr9 elicitor molecule, e.g. as provided by a *Cladosporium fulvum* race or other organism expressing Avr9 (de Wit, 1992), the amino acid and encoding nucleic acid sequences of chimaeric forms of which are given for example in WO95/18230 as SEQ ID NO 3 and in WO95/31564 as SEQ ID NO 4.

comprising 38 leucine rich repeats (LRR's).

The nucleic acid isolate, which may contain DNA encoding the amino acid sequence of SEQ ID NO 2 or SEQ ID NO 3 as genomic DNA or cDNA, may be in the form of a recombinant vector, for example a phage or cosmid vector. The DNA may be under the control of an appropriate promoter and regulatory elements for expression in a host cell, for example a plant cell. In the case of genomic DNA, this may contain its own promoter and regulatory elements and in the case of cDNA this may be under the control of an appropriate promoter and regulatory elements for expression in the host cell.

Those skilled in the art are well able to construct vectors and design protocols for recombinant gene expression. Suitable vectors can be chosen or constructed, containing appropriate regulatory sequences, including promoter sequences, terminator fragments, polyadenylation seuqences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may comprise cDNA, RNA, genomic DNA and may be wholly or partially synthetic. The term "isolate" encompasses all these possibilities.

When introducing a chosen gene construct into a cell, certain considerations must be taken into account, well known to those skilled in the art. The nucleic acid to be inserted may be assembled within a construct which contains effective regulatory elements which will drive transcription. There must be available a method of transporting the construct into the cell. Once the construct is within the cell membrane, integration into the endogenous chromosomal material may or may not occur according to different embodiments of the invention. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966), electroporation (EP 290395, WO 8706614) or other forms of direct DNA uptake (DE 4005152, WO 9012096, U.S. Pat. No. 4,684,611). Agrobacterium transformation is widely used by those skilled in the art to transform dicotyledonous species. Although Agrobacterium has been reported to be able to transform foreign DNA into some monocotyledonous species (WO 92/14828), microprojectile bombardment, electroporation and direct DNA uptake are preferred where Agrobacterium is inefficient or ineffective. Alternatively, a combination of different techniques may be employed to enhance the efficiency of the transformation process, eg. bombardment with Agrobacterium coated microparticles (EP-A-486234) or mircoprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

A Cf-2 gene and modified versions thereof (alleles, mutants and derivatives thereof), and other nucleic acid provided herein may be used to confer resistance in plants, in particular tomatoes, to a pathogen such-as *C. fulvum*. This may include cloned DNA from *Lycopersicon pimpinellifolium* which has the same chromosomal location as the Cf-2 gene or any subcloned fragment thereof. For this purpose a vector as described above may be used for the production of a transgenic plant. Such a plant may possess pathogen resistance conferred by the Cf-2 gene.

The invention thus further encompasses a host cell transformed with such a vector, especially a plant or a microbial cell. Thus, a host cell, such as a plant cell, comprising nucleic acid according to the present invention is provided. Within the cell, the nucleic acid may be incorporated within the chromosome.

A vector comprising nucleic acid according to the present invention need not include a promoter, particularly if the vector is to be used to introduce the nucleic acid into cells for recombination into the genome.

Also according to the invention there is provided a plant cell comprising, e.g. having incorporated into its genome a sequence of nucleotides as provided by the present invention, under operative control of a promoter for control of expression of the encoded polypeptide. A further aspect of the present invention provides a method of making such a plant cell involving introduction of a vector comprising the sequence of nucleotides into a plant cell. Such introduction may be followed by recombination between the vector and the plant cell genome to introduce the sequence of nucleotides into the genome. The polypeptide encoded by the introduced nucleic acid may then be expressed.

A plant which comprises a plant cell according to the invention is also provided, along with any part or clone of such a plant, seed, selfed or hybrid progeny and descendants, and any part of these, such as cuttings, seed. The invention provides any plant propagule, that is any part which may be used in reproduction or propagation, sexual or asexual, including cuttings, seed and so on.

The invention further provides a method of comprising expression from nucleic acid encoding the amino acid sequence SEQ ID NO 2 or SEQ ID NO 3, or a mutant, allele or derivative of either sequence, within cells of a plant (thereby producing the encoded polypeptide), following an earlier step of introduction of the nucleic acid into a cell of the plant or an ancestor thereof. Such a method may confer pathogen resistance on the plant. This may be used in combination with the Avr2 gene according to any of the methods described in WO91/15585 (Mogen) or, more preferably, PCT/GB95/01075 (published as WO 95/31564), or any other gene involved in conferring pathogen resistance.

The Cf-2 and Cf-9 genes function in a similar manner in that they both confer a resistance to tomato that prevents the growth of tomato leaf mould *C. fulvum*. They, however, by recognition of different Avr products and have subtle differences in the speed with which they stop growth of the pathogen and stimulate a resistance response (Hammond-Kosack and Jones 1994; Ashfield et al 1994). These differences may be exploited to optimise applications disclosed herein.

A gene stably incorporated into the genome of a plant is passed from generation to generation to descendants of the plant, cells of which decendants may express the encoded polypeptide and so may have enhanced pathogen resistance. Pathogen resistance may be determined by assessing compatibility of a pathogen (eg. *Cladosporium fulvum*) or using recombinant expression of a pathogen avirulence gene, such as Avr-2 or delivery of the Avr-2 gene product.

Sequencing of the Cf-2 gene has shown that like the Cf-9 gene it includes DNA sequence encoding leucine-rich repeat (LRR) regions and homology searching has revealed strong homologies to other genes containing LRRs. The Cf-2 and Cf-9 genes contain all the same general features and as such form a new class of disease resistance genes separate from other disease resistance genes characterised to date. As discussed in WO 95/18230, and validated herein, the presence of LRRs may be characteristic of many pathogen resistance genes and the presence of LRRs may be used in identifying further pathogen resistance genes.

Furthermore, there are some striking homologies between Cf-9 and Cf-2. These homologies may also be used to identify further resistance genes of this class, for example using oligonucleotides (e.g. a degenerate pool) designed on the basis of sequences conserved (preferably at the amino acid level) between the Cf-9 and the Cf-2 genes.

According to a further aspect, the present invention provides a method of identifying a plant pathogen resistance gene comprising use of an oligonucleotide which comprises a sequence or sequences that are conserved between pathogen resistance genes such as Cf-9 and Cf-2 to search for new resistance genes. Thus, a method of obtaining nucleic acid comprising a pathogen resistance-gene (encoding a polypeptide able to confer pathogen resistance) is provided, Comprising hybridisation of an oligonucleotide (details of which are discussed herein) or a nucleic acid molecular comprising such an oligonucleotide to target/candidate nucleic acid. Target or candidate nucleic acid may, for example, comprise a genomic or cDNA library obtainable from an organism known to encode a pathogen resistance gene. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al. 1990, Academic Press, New York.

Preferred amino acid sequences suitable for use in the design of probes or PCR primers are sequences conserved (completely, substantially-or partly) between polypeptides able to confer pathogen resistance such as those encoded by Cf-2 and Cf-9.

On the basis of amino acid sequence information, oligonucleotide probes or primers may be designed, taking into account the degeneracy of the genetic code, and, where appropriate, codon usage of the organism from the candidate nucleic acid is derived. Preferred nucleotide sequences may include those comprising or having a sequence encoding amino acids (i) SGEIPOO (SEQ ID NO: 9); (ii) YE/OGNDG (SEQ ID NO: 10); (iii) FEGHIPS (SEQ ID NO: 13); or (iv) SGEIPOOLASLTSLE (SEQ ID NO: 14), or a sequence complementary to these encoding sequences. Suitable fragments of these may be employed.

Preferred oligonucleotide sequences include:
(i) TCX-GGX-GAA/G-AAT.C.A-CCX-CAA/G-CA (SEQ ID NO: 11);
(ii) TAT/C-G/CAA/G-GGX-AAT/C-GAT/C-GGX-CTX-CG (SEQ ID NO: 15); and
(iii) CG-XAG-XCC-A/GTC-A/GTT-XCC-T/CTC/G-A/GTA (SEQ ID NO: 12).

(All sequences given 5' to 3'; see FIG. 6). Sequences (ii) and (iii) are complementary: (iii) is useful as a back (reverse) primer in PCR.

Preferably in oligonucleotide in accordance with the invention, e.g. for use in nucleic acid amplification, has about 10 or fewer codons (e.g. 6, 7 or 8), i.e. is about 30 or fewer nucleotides in length (e.g. 18, 21 or 24).

Assessment of whether or not a PCR product corresponds to a resistance genes may be conducted in various ways. A PCR band may contain a complex mix of products. Individual products may be cloned and each sreened for linkage to known disease resistance genes that are segregating in progeny that showed a polymorphism for this probe. Alternatively, the PCR product may be treated in a way that enables one to display the polymorphism on a denaturing polyacrylamide DNA sequencing gel with specific bands that are linked to the resistance gene being preselected prior to cloning. Once a candidate PCR band has been cloned and shown to be linked to a known resistance gene, it may be used to isolate clones which may be inspected for other features and homologies to Cf-9, Cf-2 or other related gene. It may subsequently be analysed by transformation to assess its function on introduction into a disease sensitive variety of the plant of interest. Alternatively, the PCR band or sequences derived by analysing it may be used to assist plant breeders in monitoring the segregation of a useful resistance gene.

These techniques are of general applicability to the identification of pathogen resistance genes in plants. Examples of the type of genes that can be identified in this way include Phytophthora resistance in potatoes, mildew resistance and rust resistance in cereals such as barley and maize, rust resistance in Antirrhinum and flax, downy mildew resistance in lettuce and Arabidopsis, virus resistance in potato, tomato and tobacco, nematode resistance in tomato, resistance to bacterial pathogens in Arabidopsis and tomato and Xanthomonas resistance in peppers.

Once a pathogen resistance gene has been identified, it may be reintroduced into plant cells using techniques well known to those skilled in the art to produce transgenic plants. According to a further aspect, the present invention provides a DNA isolate encoding the protein product of a plant pathogen resistance gene which has been identified by use of the presence therein of LRRs or, in particular, by the technique defined above. According to a yet further aspect, the invention provides transgenic plants, in particular crop plants, which have been engineered to carry pathogen resistance genes which have been identified by the presence of LRRs or by nucleic acid hybridisation as disclosed. Examples of suitable plants include tobacco, cucurbits, carrot, vegetable brassica, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus and pine.

Modifications to these and further aspects and embodiments of the present invention will be apparent to those skilled in the art. All documents mentioned herein are incorporated by reference.

As already indicated, the present invention is based on the cloning and sequencing of the tomato Cf-2 genes and this experimental work is described in more detail below with reference to the following figures.

FIG. 1 shows a physical map of the tomato Cf-2 locus generated from overlapping cosmids (38, 82, 89, 90, 92, 94, 96 and 141) isolated from the Cf-2/Cf-9 cosmid library. Also included are the modified cosmids ($112B_1$ and $112B_2$) which contain sequences derived from cosmid 94 (also known as 2.2). The extent of each cosmid and location of the Cf-2 genes are shown schematically. Also indicated is the predicted direction of transcription (arrow). The boxed regions represent expanded views of areas encoding Cf-2 genes. The open boxes show regions not sequenced, the hatched boxes show the sequenced regions.

FIGS. 2A–2E show the genomic DNA sequence of the Cf-2.1 gene (SEQ ID NO 1). Features: Nucleic acid sequence—Translation start at nucleotide 1677; translation stop at nucleotide 5012; a consensus polyadenylation signal (AATAAA) exists in the characterised sequence downstream of the translation stop starting at nucleotide 3586. Predicted Protein Sequence—primary translation product 1112 amino acids; signal peptide sequence amino acids 1–26; mature peptide amino acids 27–1112.

FIG. 3A shows Cf-2 protein amino acid sequence, designated Cf-2, 1 (SEQ ID NO 2). FIG. 3B shows the amino acid sequence encoded by the Cf-2.2 gene (SEQ ID NO. 3). Amino acids which differ between the two Cf-2 genes are underlined.

FIGS. 4A–4C show the sequence of an almost full length CDNA clone (SEQ ID NO. 4) which corresponds to the Cf2-2 gene.

FIG. 5 shows a comparison of the carboxy-terminal regions of the Cf-2 and Cf-9 genes (SEQ ID No's 5 and 6, respectively). The protein sequences are aligned according to predicted protein domains. Identical amino acid residues are indicated by bold type. FIG. 6 shows an alignment of part of the Cf-2 and Cf-9 proteins (SEQ ID NO's 7 and 8, respectively). Two identical regions are shown in bold type and are also shown as PEP SEQ 1 (SEQ ID NO. 9) and PEP SEQ 2 (SEQ ID NO. 10) respectively. OLIGO 1 (SEQ ID NO. 11) and OLIGO 2 (SEQ ID NO. 12) show the sequence of degenerate oliggonucleotides which encode these regions of protein similarity.

FIGS. 7A–7G show the primary amino acid sequence of Cf-2 (SEQ ID NO. 2) divided into domains of predicted differing functions.

Cloning of the Tomato Cf-2 Gene

The Cf-2 gene was cloned using a map-based cloning strategy similar in principle to that used for the isolation of the tomato Pto gene, described briefly earlier.

(i) Assignment of Cf- Gene-Map Locations

We have mapped several Cf genes, including Cf -2, to their chromosomal locations (Dickinson et al 1993; Jones et: al 41993; Balint-Kurti et al 1994). We showed that Cf-4 and Cf-9 map to approximately the same location on the short arm -of chromosome 1, and Cf -2 and Cf -5 map to approximately the same location on chromosome 6.

(ii) High Resolution Mapping of the Physical Location of the Cf-2 Gene

We have ordered a number of restriction fragment length polymorphism (RFLP) markers by examining the DNA isolated from recombinant tomato plants. In this way, we have assembled a detailed linkage map of the location of the Cf-2 gene on tomato chromosome 6 (Dixon et al 1995]). We determined that the Cf-2 gene maps between the RFLP markers MG112A and CT119. These RFLP markers were made available from the laboratory of S. Tanksley (Cornell). Using available YACs, also made available by the Tanksley laboratory, we have also shown that in tomato (*L. esculentum*) the physical distance between the markers MG112A and CT119 is only 40 kb. We isolated two further RFLP markers, MG112B (a weak homologue of MG112A) and SC3–8 that were shown to map to this region and as such represented candidate Cf-2 genes.

To determine more precisely the position of the Cf-2 gene, tomato crosses were set up to look for recombination between the Cf-2 and Cf-5 resistance genes. A plant that was heterozygous for both Cf -2 and Cf-5 was crossed to a *C. fulvum-sensitive* tomato line. Approximately 12,000 resulting F1 progeny were screened for resistance to *C. fulvum*, and a single sensitive plant was identified. DNA from this plant was analysed with the molecular markers which map closely to the Cf-2 gene and this plant was found to carry a chromosome that was recombinant between MG112A and CT119. This analysis strongly indicated that the RFLP marker MG112B identified DNA which mapped very closely linked to the Cf-2 gene or was the Cf-2 gene itself (Dixon et al 1996).

(iii) Isolation of Binary Cosmid Vector Clones that Carry a Genomic Cf-2 Gene

To determine whether DNA identified by the molecular marker MG112B carried the Cf-2 gene, DNA sequences were isolated from a plant that carried the Cf-2 gene and transformed into Cf-0 tomato plants.

A genomic DNA library was constructed from a stock that carried both the Cf-9 gene on chromosome 1, and the Cf-2 gene on chromosome 6, so that the library could be used for isolating both genes. The library was constructed in a binary cosmid cloning vector pCLD04541, obtained from Dr C. Dean, John Innes Centre, Colney Lane, Norwich (see also Bent et al 1994). This vector is essentially similar to pOCA18 (Olszewski et al 1988). It contains a bacteriophage lambda cos site to render the vector packageable by lambda packaging extracts and is thus a cosmid (Hohn and Collins, 1980). It is also a binary vector (van den Elzen et al 1985), so any cosmid clones that are isolated can be introduced directly into plants to test for the function of the cloned gene.

High molecular weight DNA was isolated from leaves of 6 week old greenhouse-grown plants by techniques well known to those skilled in that art (Thomas et al 1994) and partially digested with MboI restriction enzyme. The partial digestion products were size fractionated using a sucrose gradient and DNA in the size range 20–25 kilobases (kb) was ligated to BamHI digested pCLD04541 DNA, using techniques well known to those skilled in the art. After in vitro packaging using Stratagene packaging extracts, the cosmids were introduced into a tetracycline sensitive version (obtained from Stratagene) of the Stratagene *Escherichia coli* strain SURE™. Recombinants were selected using the tetracycline resistance gene on pCLD04541.

The library was randomly distributed into 144 pools containing about 1500 clones per pool, cells were grown from each pool and from 10 ml of cells, 9 ml were used for bulk plasmid DNA extractions, and 1 ml was used after addition of 0.2 ml of glycerol, to prepare a frozen stock. Plasmid DNA from the pools was isolated by alkaline lysis (Birnboim and Doly, 1979), and DNA samples were analyzed by hybridisation in "slot blots"with the molecular marker MGl12B. Pools 38, 82, 89, 90, 92, 94, 96 and 141 proved positive by this assay. "94" is also known as "2.2".

For each pool, approximately 10,000 colonies were plated out and inspected for MG112B homology by colony hybridisation with a radioactive MG112B probe, and from each pool, single clones were isolated that carried such homology. These techniques are all well known to those skilled in the art.

These clones have been further characterized by Southern blot hybridisation using a MG112B probe, and by restriction enzyme mapping. Our current assessment of the extent of contiguous DNA around MG112B, as defined by these overlapping cosmids is shown in FIG. 1. These cosmids revealed two regions with very similar restriction maps that hybridised to MG112B (now labelled MG112B$_1$ and B$_2$ respectively). Four of these cosmids (82, 89, 94, 141) were subsequently used in plant transformation experiments, selecting for plant cells transformed to kanamycin resistance, using techniques well known to those skilled in the art. Transgenic tomato and tobacco plants were produced (Fillatti et al 1987; Horsch et al 1985) with at least one of each of cosmids 82, 89, 94 and 141.

(iv) Assessment of Cosmid Function in Transgenic Tomato

The function of a putative cloned Cf-2 gene was assessed in transformed tomato by testing transformants for resistance to Avr2-carrying *C. fulvum*.

Most transgenic plants containing cosmid 94 (11 of 16) or cosmid 82 (all of 4) were resistant to *C. fulvum* carrying Avr2. All transgenic plants containing cosmid 89 or 141 were sensitive to *C. fulvum*. These data indicate that the genomic DNA which carries the Cf-2 gene is that piece which corresponds to the overlap between cosmids 82 and 94. Thus the Cf-2 gene lies in one of the regions identified by marker MG112B$_1$.

The region on cosmid 94 identified by MG112B$_2$ has many similarities with the cosmid 82/94 overlap. This region was subcloned to generate cosmid 112B$_2$ (FIG. 1) which was also transformed into a sensitive tomato line. Of the transgenic tomato plants carrying cosmid 112B$_2$, 16 of 18 were resistant to *C. fulvum* carrying Avr2. The overlap between cosmids 82 and 112B$_2$ is very small and unlikely to carry the Cf-2 gene. Additionally, the region identified as MG112B$_1$ was subcloned to generate cosmid 112B$_1$ (FIG. 1) which was transformed into a sensitive tomato line. This cosmid 112B$_1$ only contains the sequences characterised in FIG. 2 (SEQ ID NO. 1). Of the transgenic tomato carrying cosmid 112B$_1$, all (5 out of 5) were resistant to *C. fulvum* carrying Avr-2. Therefore, these data indicate the presence of 2 functional Cf-2 genes (Cf-2.1 and Cf-2.2 respectively) characterised by the molecular probe MG112B (Dixon et al 1996). The results of all transformation experiments are summarized in Table 1.

Progeny from all resistant nonpolyploid transformed plants were screened with matched races of *C. fulvum* either carrying or lacking Avr-2 (race 5,9 compared with race 2,5,9). Races of *C. fulvum* are named after the resistance genes they can overcome. All progeny were susceptible to *C. fulvum* lacking Avr-2 (race 2,5,9) whereas approximately 75% of progeny from each transformant were resistant to *C. fulvum* carrying Avr-2 (race 5,9). These data confirm the race-specific nature of the resistance genes cloned as Cf-2.

(v) DNA Sequence Analysis of the Regions Characterised by MG112B.

The DNA sequence of the 6.5 kb region representing the central core of the cosmid 82/94 overlap has been determined. Two small regions of 2.3 and 1.1 kb corresponding to the extremities of the cosmid overlap have not been sequenced (FIG. 1).

The central core sequence carries a single major open reading frame which upon conceptual translation has revealed an interesting motif (the leucine rich repeat, or LRR) that may be diagnostic of other resistance genes, as previously noted for the Cf-9 gene (WO 95/18320). The open reading frame initiates with the translation start codon (ATG) at position 1677 and finishes with the translation termination codon TAG at position 5012 with an intervening 3336 bp sequence that encodes a 1112 amino acid protein. This is the Cf-2.1 gene.

The sequence of the region labelled MG112B$_2$ carried on cosmid 112B$_2$ has also been determined. This sequence also carries a single open reading frame which differs by only 3 nucleotides from the Cf-2.1 gene sequence. Upon conceptional translation this also encodes a 1112 amino acid protein which differs by only 3 amino acids from the Cf-2.1 protein. These amino acid differences are all clustered in the carboxy-terminal region of the protein and are indicated as underlined residues in FIG. 3B (SEQ ID NO. 3). We therefore designate this to be Cf-2.2.

An almost full length cDNA clone (SEQ ID NO. 4) has been isolated corresponding to the Cf-2 gene (FIG. 4). This confirms the predicted amino acid sequence of the Cf-2 genes as it is colinear with the genomic sequence through the entire open reading frame. The cDNA clone lacks the most 5' sequences including any untranslated leader sequence and the codon encoding the initiator methionine. The first full codon of this CDNA encodes for Valine which is amino acid number 4. A single intron of 182 bases exists in the 3' untranslated sequences (Dixon et al 1996).

Genbank accession numbers for the sequences reported within are U42444 for Cf-2.1 and U42445 for Cf-2.2.

(vi) Identification of a Leucine-rich Repeat Region in Cf-2.

A genomic DNA sequence of the Cf-2.1 gene is shown in FIG. 2 (SEQ ID NO. 1). The deduced amino acid sequence of the Cf-2 protein is shown in FIG. 3A (SEQ ID NO. 2).

Homology searching of the resulting sequence against sequences in the databases at the US National Centre of Biological Information (NCBI) reveals strong homologies to other genes that contain leucine rich repeat regions (LRRs). The Cf-2 gene identifies Cf-9 with a blast score of 483. Other homologies include the Arabidopsis genes TMK1 (Chang et al 1992), TMKL1 (Valon et al 1993), RLK5 (Walker, 1993), as well as expressed sequences with incomplete sequence and unknown function (e.g. *Arabidopsis thaliana* transcribed sequence [ATTS] 1447). The presence of LRRs has been observed in other genes, many of which probably function as receptors (see Chang et al [1992] for further references).

The TMK1 and RLK5 genes have structures which suggest they encode transmembrane serine/threonine kinases and carry extensive LRR regions. As yet no known function has been assigned to them. Disease resistance genes are known to encode gene products which recognize pathogen products and subsequently initiate a signal transduction chain leading to a defence response. It is known that another characterized disease resistance gene (Pto) is a protein kinase (Martin et al 1993). However, in Cf-2 there is no apparent protein kinase domain based on genomic DNA and cDNA sequence analysis.

The predicted Cf-2 amino acid sequence can be divided into 7 domains (FIG. 7).

Domain A is a 26 amino acid probable signal peptide.

Domain B is a 37 amino acid region with some homology to polygalacturonase inhibitor proteins.

Domain C is a 930 amino acid comprising 33 perfect copies and 5 imperfect copies of a 24 amino acid leucine rich repeat (LRR).

Domain D is a 30 amino acid domain with some homology to polygalacturonase inhibitor proteins.

Domain E is a 28 amino acid domain rich in negatively charged residues.

Domain F is a 24 amino acid hydrophobic domain encoding a putative transmembrane domain.

Domain G is a 37 amino acid domain rich in positively charged residues.

Domains E, F and G together comprise a likely membrane anchor.

The Cf-2 and Cf-9 proteins are predicted to have the same general features in that they can both be sub-divided into the above 7 domains. They are, however, very different in length, 1112 verses 863 amino acids respectively. The majority of this size difference resides in the number of LRRs in domains C. Although the LLRs are characterised by specific conserved amino acids (mainly leucine), they are generally spaced apart such that no block of conserved amino acids exists. Additionally, leucine can be encoded by 6 different codons and as a result it would be difficult to exploit the similarities of the conserved amino acids in the LLR domain at the level of DNA hybridisation to identify new related genes. Indeed, at the level of genomic Southern hybridisation the Cf-2 and Cf-9 genes did not identify each other under the conditions we used.

(vii) Comparison of the Amino Acid Sequence of Cf-2 and Cf -9

Comparison of the amino acid sequence of Cf-2 and Cf-9 shows a remarkable degree of homology at the end of Domain C and in Domain D. These are shown in bold in FIG. 6. Regions of Cf-2 such as the sequence F E G H I P S (SEQ ID NO. 13) starting at position 915 and the sequence S G E I P Q Q L A S L T F L E (SEQ ID NO. 14) starting at position 965 are absolutely identical to Cf-9. Other regions of identity or strong conservation also exist. Since Cf-2 and Cf-9 are on different chromosomes, it seems likely that they did not diverge recently. This conservation then suggests functional conservation due to selection of the maintenance of an association between the amino acids in Cf-9 and Cf-2 and some other protein required for Cf-9 or Cf-2 to provide disease resistance.

Accordingly, these homologies may be used in the isolation of further disease resistance genes. Using techniques well known to those skilled in the art these sequences and fragments thereof may be used to design oligonucleotide probes/primers for the purpose of isolating further disease resistance genes that carry these amino acid sequence motifs.

For example, based upon the identities between the Cf-2 and Cf-9 genes (FIGS. 5 and 6), synthetic degenerate oligonucleotide primers like those indicated in FIG. 6 might be produced. These primers correspond to the different DNA sequences which potentially encode amino acids conserved between the Cf-2 and Cf-9 polypeptides. These synthetic oligonucleotide primers may be used in a PCR to identify related sequences from any species which contains them.

TABLE 1

| Line | Cosmid 94 | Cosmid 82 | Cosmid 89 | Cosmid 141 | Cosmid 112B$_1$ | Cosmid 112B$_2$ |
|---|---|---|---|---|---|---|
| A | S | R | S | S | R | R |
| B | S | R | S | S | R | R |
| C | R | R | S | S | R | R |
| D | R | R | S | S | R | R |
| E | R |   | S | S | R | R |
| F | R |   | S | S |   | R |
| G | R |   | S |   |   | R |
| H | R |   | S |   |   | R |
| I | R |   | S |   |   | R |
| J | R |   |   |   |   | R |
| K | R |   |   |   |   | R |
| L | R |   |   |   |   | R |
| M | S |   |   |   |   | R |
| N | R |   |   |   |   | N |
| O | S |   |   |   |   | R |
| P | S |   |   |   |   | R |
| Q |   |   |   |   |   | S |
| R |   |   |   |   |   | R |

The reponse of transgenic tomato plants (primary transformants) carrying different cosmids. Tomato transformants were tested for resistance (R) or susceptibility (S) to a race of C. fulvum carrying Avr-2 (Race 4 GUS).

REFERENCES

1. Ashfield T, et al., (1994) Mol.Plant.Mic.Int. 7:645–657.
2. Balint-Kurti P, et al., Theor.App.Genet. (1994) 88 pp 691–700.
3. Bent, A. F., et al., (1994) Science 265:1856.
4. Birnboim, H. C. and Doly, J. (1979) Nucl. Acids. Res. 7:1513–1520.
5. Chang C, et al., (1992) The Plant Cell 4:1263–1271.
6. De Wit, PJGM (1992) Ann.Rev.Phytopathol. 30:391–418.
7. Dickinson M, et al., (1993) Mol.Plant Mic.Int. 6:341–347.
8. Dixon M S, et al. (1995). High resolution mapping of the physical location of the Cf-2 gene. Mol.Plant.Mic.Int. 8:200–206.
9. Dixon M S, et al., (1996). Cell 84:451–459.
10. Fillatti J J, et al. (1987). Bio/technol. 5:726–730.
11. Flor H H (1971). Ann.Rev.Phytopathol. 9:275–296.
12. Gabriel D W, et al. (1990). Ann.Rev.Phytopathol. 28:365–391.
13. Hammond-Kosack K E, et al. (1994) Mol. Plant.Mic.Int. 7: 58–70.
14. Hohn B. et al. (1980). Gene 11:291–298.
15. Horsch R B, et al. (1985). Science (Wash.). 227:1229–1231.
16. Johal G S, et al. (1992). Science (Wash.). 258:985–987.
17. Jones D A, et al. (1993). Mol.Plant Mic.Int. 6:348–357.
18. Jones J D G, et al. (1992). Transgen. Res. 1:285–297.
19. Jones D A, et al. (1994). Science (Wash. 266:789–793.
20. Keen N T (1992). Ann.Rev.Gen. 24:447–463.
21. Long S R (1993). Cell 73:921–935.
22. Martin G B, et al. (1993). Science 262:1432–1436.
23. Mindrinos M, et al. (1994). Cell 78:1089–1055.
24. Olszewski N E, et al. (1988). Nucl. Acids. Res 16:10765–10782.
25. Stein J C, et al. (1991). Proc.Natl.Acad.Sci.USA 88:8816–8820.
[26]. Thomas C M, et al. (1994). Mol. & Gen.Genet. 242:573–585.
27. Valon C, et al. (1993). Pl.Molec.Biol. 23:415–421.
28. van den Elzen P, et al. (1985). Plant. Mol. Biol. 5:149–154.
29. Walker J C (1993). Plant Journal 3:451–456.
30. Whitham S, et al. (1994). Cell 78:1011–1115.

What is claimed is:

1. An isolated nucleic acid
comprising a sequence of nucleotides encoding a pathogen resistance polypeptide whose expression in a plant can cause activation of a defense response in the plant
wherein said activation occurs upon contact of the plant with a pathogen or corresponding elicitor molecule,
wherein the polpeptide comprises the sequence of amino acids shown in FIG. 3A (SEQ ID NO: 2) or FIG. 3B (SEQ ID NO: 3).

2. An isolated vector comprising the nucleic acid according to claim 1.

3. A vector according to claim 2 further comprising regulatory sequences for expression of said polypeptide.

4. A host cell comprising a heterologous polynucleotide comprising the nucleic acid according to claim 1.

5. A host cell according to claim 4 which is a microbial cell.

6. A host cell according to claim 5 which is a plant cell.

7. A method which comprises introducing the nucleic acid according to claim 1 into a host cell.

8. A method according to claim 7 wherein the host cell is a plant or microbial cell.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
       (A) LENGTH: 6471 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (vi) ORIGINAL SOURCE:
       (A) ORGANISM: Tomato
       (B) STRAIN: Cf2

(ix) FEATURE:
       (A) NAME/KEY: mat_peptide
       (B) LOCATION:1754..5012

(ix) FEATURE:
       (A) NAME/KEY: sig_peptide
       (B) LOCATION:1677..1753

(xi) SEQUENCE DESCRIPTION: SEQ ID NO: 1:

```
CTCGAGTTCG GAACCTAAAA GGTATAAAAT ATTAATAAAA ATTTTAAAAT GGTATATCAA      60
TTTTTATATT AACCAAAACG TCAAAATCGC TGAAACAACA GCGATTTCCT TCACCGGAAA     120
AAGCAAAATC GCTACTACTG CAGCGATTTT GCAAAATGTA ACTTTTTTTT AAAAAAATGC     180
ATATTTCTT ATAAGCTATA TATTTGAATT TCAAAAAAAA TATTTGAAAA TCAATAAAAT      240
TTGTTTTTCC TACGATTTTC TTTTTAAAAT TCTTTTTTTG GAAAATCCCT ACCTAGGCAG     300
CGATTTCCAT TTTTAATTTT TTTTAAATAA AAGGCAGCGA TTTTCGAAAA AAAAAATTTT     360
AAAAAAATT GAAAAGTCG CTGCCTAGGT AGCGATTTGA ATTTTTTTAA AAAATGTTAT       420
ATTTTGCAAA ATCGTTGCAG TAGCAACGAT TTTGCTTTTT TTGGAGGAAA TCGCTGTTGT     480
TCCAGCGATT TTGCCGTTTT GGTTAATATA AAATTTTATA TAACGTTTTG AAATTTTTGT     540
TAATATTTTA TAACTTTTAG GCTCCGGACT CAAGATTACT CCCTCTATCT TAGTTTATAA     600
TGCATAGTCT GAATTTTGAA GAGCCAAATA GTTAATTTT CGCCATAAAT TCAGACATGA     660
AATCTTTAAA AAAGTTTAAA TAAAATTTGT ATATGTTGAA ACTACAGAAA AAGTATTATA     720
ATTCACGATA ATTTATTCAC AAGCCATCGT CGGAGTGATC GCGAGTGAAG TGAAAGAATT     780
GGAGTTTTTG ATATCCAGAA TCCATCTTGA GAGGTTGAGA TATCTTAATC TATCTCCAAT     840
AAAAAAAAAC TATTAATATC CAATTTTCTT GAAGGCCATT ACCTATTCCG ACAAATTCCA     900
CAAGATACTT CATCATATAA AAAAATAATC TCCGTGAAGA AATTCTTTTA TTTGGAAAAT     960
CGATTTTAGA GTCATTGCAA TTTAATTTTA TCAAAATATT TGAGCATGAA AAATTTGAAA    1020
TGGAGGTGTC ATAAAAATAA AATACCCTTT AAAACACGGC TTTATTGAGT TGACGATAGT    1080
TCAAGTAGGG AAAATAAATA ACTTATTAAT TGAATATAAA ACTTGCAAGA AAAAAGTGAT    1140
ATTCAAATTT AATTCTGACC ATTATCTCTT GATATTCTTT GCTCTTCATT TATTTGAATA    1200
TTCATTTTTC AAAAGTTCCA CGTCATAAGA CATCAAATAT CAAGTAGGTC CCATAAAAAT    1260
AAAATACCCT TCTCAACATG ACAAAGAAAG ATTGAAAAAT GACTAACATT TTCTCAAAGA    1320
CAAAAACAAA ACATGTGAGA GAAGACATTA CGAATCATCA TAATCTCTGA GACTGAGAAT    1380
TGTTAGATAT GGTCCACTAC TGTAGAGATG AGAATTTTGA ACCAAATGTA TTATACACTA    1440
AGAGTGGTCA TGATCATTGT GTGATAACAA AACTATTTTG GCAACTTTGA CTCAGTCCTT    1500
GGCTAAATTA GACCTCTAAC ACAAAACAAT CCAAAAGTTG ACTTGAGAAT GACAACATTT    1560
TCTTCCCTGA TAGCAACCAA ATTAGCAAAT TTGGAAAAAA CGCGTGTCTT GTTGATCTTT    1620
AATTAGTATA AGTTACGTAC AATATCCTAT TGAATTGGAA ACAATAAACT CAAACTATGA    1680
TGATGGTTTC TAGAAAAGTA GTCTCTTCAC TTCAGTTTTT CACTCTTTTC TACCTCTTTA    1740
CAGTTGCATT TGCTTCGACT GAGGAGGCAA CTGCCCTCTT GAAATGGAAA GCAACTTTCA    1800
AGAACCAGAA TAATTCCTTT TTGGCTTCAT GGATTCCAAG TTCTAATGCA TGCAAGGACT    1860
GGTATGGAGT TGTATGCTTT AATGGTAGGG TAAACACGTT GAATATTACA AATGCTAGTG    1920
TCATTGGTAC ACTCTATGCT TTTCCATTTT CATCCCTCCC TTCTCTTGAA AATCTTGATC    1980
TTAGCAAGAA CAATATCTAT GGTACCATTC CACCTGAGAT TGGTAATCTC ACAAATCTTG    2040
TCTATCTTGA CTTGAACAAC AATCAGATTT CAGGAACAAT ACCACCACAA ATCGGTTTAC    2100
TAGCCAAGCT TCAGATCATC CGCATATTTC ACAATCAATT AAATGGATTT ATTCCTAAAG    2160
AAATAGGTTA CCTAAGGTCT CTTACTAAGC TATCTTTGGG TATCAACTTT CTTAGTGGTT    2220
CCATTCCTGC TTCAGTGGGG AATCTGAACA ACTTGTCTTT TTTGTATCTT TACAATAATC    2280
AGCTTTCTGG CTCTATTCCT GAAGAAATAA GTTACCTAAG ATCTCTTACT GAGCTAGATT    2340
```

```
TGAGTGATAA TGCTCTTAAT GGCTCTATTC CTGCTTCATT GGGGAATATG AACAACTTGT    2400

CTTTTTTGTT TCTTTATGGA AATCAGCTTT CTGGCTCTAT TCCTGAAGAA ATATGTTACC    2460

TAAGATCTCT TACTTACCTA GATTTGAGTG AGAATGCTCT TAATGGCTCT ATTCCTGCTT    2520

CATTGGGGAA TTTGAACAAC TTGTCTTTTT TGTTTCTTTA TGGAAATCAG CTTTCTGGCT    2580

CTATTCCTGA AGAAATAGGT TACCTAAGAT CTCTTAATGT CCTAGGTTTG AGTGAGAATG    2640

CTCTTAATGG CTCTATTCCT GCTTCATTGG GGAATCTGAA AAACTTGTCT AGGTTGAATC    2700

TTGTTAATAA TCAGCTTTCT GGCTCTATTC CTGCTTCATT GGGGAATCTG AACAACTTGT    2760

CTATGTTGTA TCTTTACAAT AACCAGCTTT CTGGCTCTAT TCCTGCTTCA TTGGGGAATC    2820

TGAACAACTT GTCTATGTTG TATCTTTACA ATAATCAGCT TTCTGGCTCT ATTCCTGCTT    2880

CATTGGGGAA TCTGAACAAC TTGTCTAGGT TGTATCTCTA CAATAATCAG CTTTCTGGCT    2940

CTATTCCTGA AGAAATAGGT TACTTGAGTT CTCTTACTTA TCTAGATTTG AGTAATAACT    3000

CCATTAATGG ATTTATTCCT GCTTCATTTG GCAATATGAG CAACTTGGCT TTTTTGTTTC    3060

TTTATGAAAA TCAGCTTGCT AGCTCTGTTC CTGAAGAAAT AGGTTACCTA AGGTCTCTTA    3120

ATGTCCTTGA TTTGAGTGAG AATGCTCTTA ATGGCTCTAT TCCTGCTTCA TTCGGGAATT    3180

TGAACAACTT GTCTAGGTTG AATCTTGTTA ATAATCAGCT TTCTGGCTCT ATTCCTGAAG    3240

AAATAGGTTA CCTAAGGTCT CTTAATGTCC TTGATTTGAG TGAGAATGCT CTTAATGGCT    3300

CTATTCCTGC TTCATTCGGG AATTTGAACA ACTTGTCTAG GTTGAATCTT GTTAATAATC    3360

AGCTTTCTGG CTCTATTCCT GAAGAAATAG GTTACCTAAG ATCTCTTAAT GACCTAGGTT    3420

TGAGTGAGAA TGCTCTTAAT GGCTCTATTC CTGCTTCATT GGGGAATCTG AACAACTTGT    3480

CTATGTTGTA TCTTTACAAT AATCAGCTTT CTGGCTCTAT TCCTGAAGAA ATAGGTTACT    3540

TGAGTTCTCT TACTTATCTA TCTTTGGGTA ATAACTCTCT TAATGGACTT ATTCCTGCTT    3600

CATTTGGCAA TATGAGAAAT CTGCAAGCTC TGATTCTCAA TGATAACAAT CTCATTGGGG    3660

AAATTCCTTC ATCTGTGTGC AATTTGACAT CACTGGAAGT GTTGTATATG CCGAGAAACA    3720

ATTTGAAGGG AAAAGTTCCG CAATGTTTGG GTAATATCAG TAACCTTCAG GTTTTGTCGA    3780

TGTCATCTAA TAGTTTCAGT GGAGAGCTCC CTTCATCTAT TTCCAATTTA ACATCACTAC    3840

AAATACTTGA TTTTGGCAGA AACAATCTGG AGGGAGCAAT ACCACAATGT TTGGCAATA     3900

TTAGTAGCCT CGAGGTTTTT GATATGCAGA ACAACAAACT TTCTGGGACT CTTCCAACAA    3960

ATTTTAGCAT TGGATGTTCA CTGATAAGTC TCAACTTGCA TGGCAATGAA CTAGAGGATG    4020

AAATCCCTCG GTCTTTGGAC AATTGCAAAA AGCTGCAAGT TCTTGATTTA GGAGACAATC    4080

AACTCAACGA CACATTTCCC ATGTGGTTGG GAACTTTGCC AGAGCTGAGA GTTTTAAGGT    4140

TGACATCGAA TAAATTGCAT GGACCTATAA GATCATCAAG GGCTGAAATC ATGTTTCCTG    4200

ATCTTCGAAT CATAGATCTC TCTCGCAATG CATTCTCGCA AGACTTACCA ACGAGTCTAT    4260

TTGAACATTT GAAAGGGATG AGGACAGTTG ATAAAACAAT GGAGGAACCA AGTTATGAAA    4320

GCTATTACGA TGACTCGGTG GTAGTTGTGA CAAAGGGATT GGAGCTTGAA ATTGTGAGAA    4380

TTTTGTCTTT GTACACAGTT ATCGATCTTT CAAGCAACAA ATTTGAAGGA CATATTCCTT    4440

CTGTCCTGGG AGATCTCATT GCGATCCGTA TACTTAATGT ATCTCATAAT GCATTGCAAG    4500

GCTATATACC ATCATCACTT GGAAGTTTAT CTATACTGGA ATCACTAGAC CTTTCGTTTA    4560

ACCAACTTTC AGGAGAGATA CCACAACAAC TTGCTTCTCT TACGTTTCTT GAATTCTTAA    4620

ATCTCTCCCA CAATTATCTC CAAGGATGCA TCCCTCAAGG ACCTCAATTC CGTACCTTTG    4680
```

```
AGAGCAATTC ATATGAAGGT AATGATGGAT TACGTGGATA TCCAGTTTCA AAAGGTTGTG    4740

GCAAAGATCC TGTGTCAGAG AAAAACTATA CAGTGTCTGC GCTAGAAGAT CAAGAAAGCA    4800

ATTCTGAATT TTTCAATGAT TTTTGGAAAG CAGCTCTGAT GGGCTATGGA AGTGGACTGT    4860

GTATTGGCAT ATCCATGATA TATATCTTGA TCTCGACTGG AAATCTAAGA TGGCTTGCAA    4920

GAATCATTGA AAAACTGGAA CACAAAATTA TCATGCAAAG GAGAAAGAAG CAGCGAGGTC    4980

AAAGAAATTA CAGAAGAAGA ATAATCACT  TCTAGACAAG TTACCAATAC AGAAAGATTT    5040

GATTTCAGAA CTTCAGGTAT TCACGCTAAG CTCTAACACT TATCTTTTTT AGTTTATTCT    5100

AACAACTAAT ATATGGTTTT TTTTTATCAA CAAATACTTA TTAAGGCTTG ATACAAATTG    5160

CTATAATCAC TTGGAAGCTG TGATATATAA CAAAGCCTAA AAATTTATAG TTGTGTGACT    5220

CACTTTCTTA TTTTTCAGAT TTTCAGGAGC CAAGAATTAG AAGACGCTGG TGTAAAGGAT    5280

TTGCTTCTTC CTATGTTGCA GCTTATGATT GTTGGATTTG ATTTTTAGTT TTATAAGGTT    5340

TTCTTCAGTT GGGAAAATGT AATATTTTGA ATTTTGATGA TATATAATAA ATGTTGTGTA    5400

TTGAATGATG TGTATGCATT TCTCGGATCA ATAATACTCA CCTCAAAGAA TCTAAGAGAG    5460

TTAGCGCACG ATAGAAGATA GAACATACAA AGAAGAATAC ATTACAACCT TGGGCTTGGT    5520

TATCTTACAC CCCAAAGCTT GTTATTATGG AAGGAAAGGC CAAGTTTTAT TTTTAGATAT    5580

GGGGAGCCTT GGCGTGCTGG TAAGGTTGTA GTGGATAAGG TAACTTCTCC TGTTAATGAA    5640

TTGAATGATC ATAGCAGAGA TGTGTTTAAA ATTTCTGTTG TATTAGTTTG TAATATTTGG    5700

AGGTCTTAAA TTGAACAGAT GCACATCTGT TCGTGAAAGA GCATGACTAT TCTTATAAGT    5760

CAACTCTCAA GTTCTATAAA TATAAGGACT CCTAAAGTAG CATAAGAAAA AACTGCAGTA    5820

TACTAAGGCG TTGTTGGATC CTGAAGGGAA TTGCTGGTAA CCCCCTAAAC AACATACGTT    5880

ATATTGGTGG GGGGTAGAAG GTACCCAGTG AAATAATCTA GGTTTGCATA GGTTGCTCTG    5940

CAAACAACAA TTATTAAACA AAATCCACAC ACACTAGCAC ATGAGAGTAA AAAATTTAAT    6000

GACGAGATGA AAGAAACTCA CGCCAAGATG GACTTTATCA AACAACAAAT ACATTGTTTG    6060

TACCTTTTGG ACAACCATTT ATCACTCAAA GAAGATCAAG GATTGATGCA TTACATCGTT    6120

CTTGGAACAA AATTATGTAC ATAAAACTTA CAGGAATCAT GTTTTGTGTG TGGTAAAACT    6180

CCATAAGGAC TAGTCCAAGA TACTGAGATC AAGGATTTCT AAGTGCAGCC AATCTCTTCT    6240

CCAGTTCATC GATCCCCGAA CTGCCAGCAC GAAAGCACAA CAACAAAATG TACATGAGCG    6300

AGTTACTGAG ATCAAAGAGC ATGAAAAAAG GCACTTCATA CTAATATGAT AACTTCATAC    6360

TAATATGATA CAATTATTTA CAGGAAGAAA AGAAGAATAG GAAACCGAAC CGCAACATAC    6420

TTTATCTATT AACGAGCAGT GCACTCAAGA TAACTAGTAT TTTTGCTCGA G             6471
```

(2) INFORMATION FOR SEQ ID NO: 2:

(i) SEQUENCE CHARACTERISTICS:
        (A) LENGTH: 1112 amino acids
        (B) TYPE: amino acid
        (C) STRANDEDNESS: <Unknown>
        (D) TOPOLOGY: linear (ii) MOLECULE TYPE: protein (iii) HYPOTHETICAL: YES (vi) ORIGINAL SOURCE:
        (A) ORGANISM: Tomato
        (B) STRAIN: Cf2

(xi) SEQUENCE DESCRIPTION: SEQ ID NO: 2:

-continued

```
Met Met Met Val Ser Arg Lys Val Val Ser Leu Gln Phe Phe Thr
1               5                   10                  15

Leu Phe Tyr Leu Phe Thr Val Ala Phe Ala Ser Thr Glu Glu Ala Thr
            20                  25                  30

Ala Leu Leu Lys Trp Lys Ala Thr Phe Lys Asn Gln Asn Asn Ser Phe
                35                  40                  45

Leu Ala Ser Trp Ile Pro Ser Ser Asn Ala Cys Lys Asp Trp Tyr Gly
            50                  55                  60

Val Val Cys Phe Asn Gly Arg Val Asn Thr Leu Asn Ile Thr Asn Ala
65                      70                  75                  80

Ser Val Ile Gly Thr Leu Tyr Ala Phe Pro Phe Ser Ser Leu Pro Ser
                85                  90                  95

Leu Glu Asn Leu Asp Leu Ser Lys Asn Asn Ile Tyr Gly Thr Ile Pro
                100                 105                 110

Pro Glu Ile Gly Asn Leu Thr Asn Leu Val Tyr Leu Asp Leu Asn Asn
            115                 120                 125

Asn Gln Ile Ser Gly Thr Ile Pro Pro Gln Ile Gly Leu Leu Ala Lys
            130                 135                 140

Leu Gln Ile Ile Arg Ile Phe His Asn Gln Leu Asn Gly Phe Ile Pro
145                 150                 155                 160

Lys Glu Ile Gly Tyr Leu Arg Ser Leu Thr Lys Leu Ser Leu Gly Ile
                165                 170                 175

Asn Phe Leu Ser Gly Ser Ile Pro Ala Ser Val Gly Asn Leu Asn Asn
            180                 185                 190

Leu Ser Phe Leu Tyr Leu Tyr Asn Asn Gln Leu Ser Gly Ser Ile Pro
            195                 200                 205

Glu Glu Ile Ser Tyr Leu Arg Ser Leu Thr Glu Leu Asp Leu Ser Asp
            210                 215                 220

Asn Ala Leu Asn Gly Ser Ile Pro Ala Ser Leu Gly Asn Met Asn Asn
225                 230                 235                 240

Leu Ser Phe Leu Phe Leu Tyr Gly Asn Gln Leu Ser Gly Ser Ile Pro
            245                 250                 255

Glu Glu Ile Cys Tyr Leu Arg Ser Leu Thr Tyr Leu Asp Leu Ser Glu
            260                 265                 270

Asn Ala Leu Asn Gly Ser Ile Pro Ala Ser Leu Gly Asn Leu Asn Asn
            275                 280                 285

Leu Ser Phe Leu Phe Leu Tyr Gly Asn Gln Leu Ser Gly Ser Ile Pro
            290                 295                 300

Glu Glu Ile Gly Tyr Leu Arg Ser Leu Asn Val Leu Gly Leu Ser Glu
305                 310                 315                 320

Asn Ala Leu Asn Gly Ser Ile Pro Ala Ser Leu Gly Asn Leu Lys Asn
            325                 330                 335

Leu Ser Arg Leu Asn Leu Val Asn Asn Gln Leu Ser Gly Ser Ile Pro
            340                 345                 350

Ala Ser Leu Gly Asn Leu Asn Asn Leu Ser Met Leu Tyr Leu Tyr Asn
            355                 360                 365

Asn Gln Leu Ser Gly Ser Ile Pro Ala Ser Leu Gly Asn Leu Asn Asn
            370                 375                 380

Leu Ser Met Leu Tyr Leu Tyr Asn Asn Gln Leu Ser Gly Ser Ile Pro
385                 390                 395                 400

Ala Ser Leu Gly Asn Leu Asn Asn Leu Ser Arg Leu Tyr Leu Tyr Asn
            405                 410                 415

Asn Gln Leu Ser Gly Ser Ile Pro Glu Glu Ile Gly Tyr Leu Ser Ser
```

-continued

```
                420                 425                 430
Leu Thr Tyr Leu Asp Leu Ser Asn Asn Ser Ile Asn Gly Phe Ile Pro
            435                 440                 445

Ala Ser Phe Gly Asn Met Ser Asn Leu Ala Phe Leu Phe Leu Tyr Glu
    450                 455                 460

Asn Gln Leu Ala Ser Ser Val Pro Glu Glu Ile Gly Tyr Leu Arg Ser
465                 470                 475                 480

Leu Asn Val Leu Asp Leu Ser Glu Asn Ala Leu Asn Gly Ser Ile Pro
            485                 490                 495

Ala Ser Phe Gly Asn Leu Asn Asn Leu Ser Arg Leu Asn Leu Val Asn
    500                 505                 510

Asn Gln Leu Ser Gly Ser Ile Pro Glu Glu Ile Gly Tyr Leu Arg Ser
    515                 520                 525

Leu Asn Val Leu Asp Leu Ser Glu Asn Ala Leu Asn Gly Ser Ile Pro
    530                 535                 540

Ala Ser Phe Gly Asn Leu Asn Asn Leu Ser Arg Leu Asn Leu Val Asn
545                 550                 555                 560

Asn Gln Leu Ser Gly Ser Ile Pro Glu Glu Ile Gly Tyr Leu Arg Ser
            565                 570                 575

Leu Asn Asp Leu Gly Leu Ser Glu Asn Ala Leu Asn Gly Ser Ile Pro
            580                 585                 590

Ala Ser Leu Gly Asn Leu Asn Asn Leu Ser Met Leu Tyr Leu Tyr Asn
    595                 600                 605

Asn Gln Leu Ser Gly Ser Ile Pro Glu Glu Ile Gly Tyr Leu Ser Ser
    610                 615                 620

Leu Thr Tyr Leu Ser Leu Gly Asn Asn Ser Leu Asn Gly Leu Ile Pro
625                 630                 635                 640

Ala Ser Phe Ala Asn Met Arg Asn Leu Gln Ala Leu Ile Leu Asn Asp
            645                 650                 655

Asn Asn Leu Ile Gly Glu Ile Pro Ser Ser Val Cys Asn Leu Thr Ser
            660                 665                 670

Leu Glu Val Leu Tyr Met Pro Arg Asn Asn Leu Lys Gly Lys Val Pro
    675                 680                 685

Gln Cys Leu Gly Asn Ile Ser Asn Leu Gln Val Leu Ser Met Ser Ser
    690                 695                 700

Asn Ser Phe Ser Gly Glu Leu Pro Ser Ser Ile Ser Asn Leu Thr Ser
705                 710                 715                 720

Leu Gln Ile Leu Asp Phe Gly Arg Asn Asn Leu Glu Gly Ala Ile Pro
            725                 730                 735

Gln Cys Phe Gly Asn Ile Ser Ser Leu Glu Val Phe Asp Met Gln Asn
            740                 745                 750

Asn Lys Leu Ser Gly Thr Leu Pro Thr Asn Phe Ser Ile Gly Cys Ser
    755                 760                 765

Leu Ile Ser Leu Asn Leu His Gly Asn Glu Leu Glu Asp Glu Ile Pro
    770                 775                 780

Arg Ser Leu Asp Asn Cys Lys Lys Leu Gln Val Leu Asp Leu Gly Asp
785                 790                 795                 800

Asn Gln Leu Asn Asp Thr Phe Pro Met Trp Leu Gly Thr Leu Pro Glu
            805                 810                 815

Leu Arg Val Leu Arg Leu Thr Ser Asn Lys Leu His Gly Pro Ile Arg
            820                 825                 830

Ser Ser Arg Ala Glu Ile Met Phe Pro Asp Leu Arg Ile Ile Asp Leu
    835                 840                 845
```

```
Ser Arg Asn Ala Phe Ser Gln Asp Leu Pro Thr Ser Leu Phe Glu His
    850                 855                 860

Leu Lys Gly Met Arg Thr Val Asp Lys Thr Met Glu Glu Pro Ser Tyr
865                 870                 875                 880

Glu Ser Tyr Tyr Asp Asp Ser Val Val Val Thr Lys Gly Leu Glu
                885                 890                 895

Leu Glu Ile Val Arg Ile Leu Ser Leu Tyr Thr Val Ile Asp Leu Ser
            900                 905                 910

Ser Asn Lys Phe Glu Gly His Ile Pro Ser Val Leu Gly Asp Leu Ile
            915                 920                 925

Ala Ile Arg Ile Leu Asn Val Ser His Asn Ala Leu Gln Gly Tyr Ile
            930                 935                 940

Pro Ser Ser Leu Gly Ser Leu Ser Ile Leu Glu Ser Leu Asp Leu Ser
945                 950                 955                 960

Phe Asn Gln Leu Ser Gly Glu Ile Pro Gln Gln Leu Ala Ser Leu Thr
            965                 970                 975

Phe Leu Glu Phe Leu Asn Leu Ser His Asn Tyr Leu Gln Gly Cys Ile
            980                 985                 990

Pro Gln Gly Pro Gln Phe Arg Thr Phe Glu Ser Asn Ser Tyr Glu Gly
            995                 1000                1005

Asn Asp Gly Leu Arg Gly Tyr Pro Val Ser Lys Gly Cys Gly Lys Asp
    1010                1015                1020

Pro Val Ser Glu Lys Asn Tyr Thr Val Ser Ala Leu Glu Asp Gln Glu
1025                1030                1035                1040

Ser Asn Ser Glu Phe Phe Asn Asp Phe Trp Lys Ala Ala Leu Met Gly
            1045                1050                1055

Tyr Gly Ser Gly Leu Cys Ile Gly Ile Ser Met Ile Tyr Ile Leu Ile
            1060                1065                1070

Ser Thr Gly Asn Leu Arg Trp Leu Ala Arg Ile Ile Glu Lys Leu Glu
            1075                1080                1085

His Lys Ile Ile Met Gln Arg Arg Lys Lys Gln Arg Gly Gln Arg Asn
            1090                1095                1100

Tyr Arg Arg Arg Asn Asn His Phe
1105                1110

(2) INFORMATION FOR SEQ ID NO: 3:

(i) SEQUENCE CHARACTERISTICS:
        (A) LENGTH: 1112 amino acids
        (B) TYPE: amino acid
        (C) STRANDEDNESS: <Unknown>
        (D) TOPOLOGY: linear (ii) MOLECULE TYPE: protein (iii) HYPOTHETICAL: YES (vi) ORIGINAL SOURCE:
         (A) ORGANISM: Tomato
         (B) STRAIN: Cf2

(xi) SEQUENCE DESCRIPTION: SEQ ID NO: 3:

Met Met Met Val Ser Arg Lys Val Val Ser Ser Leu Gln Phe Phe Thr
1               5                   10                  15

Leu Phe Tyr Leu Phe Thr Val Ala Phe Ala Ser Thr Glu Glu Ala Thr
            20                  25                  30

Ala Leu Leu Lys Trp Lys Ala Thr Phe Lys Asn Gln Asn Asn Ser Phe
            35                  40                  45
```

-continued

```
Leu Ala Ser Trp Ile Pro Ser Ser Asn Ala Cys Lys Asp Trp Tyr Gly
 50                  55                  60

Val Val Cys Phe Asn Gly Arg Val Asn Thr Leu Asn Ile Thr Asn Ala
 65                  70                  75                  80

Ser Val Ile Gly Thr Leu Tyr Ala Phe Pro Phe Ser Ser Leu Pro Ser
                 85                  90                  95

Leu Glu Asn Leu Asp Leu Ser Lys Asn Asn Ile Tyr Gly Thr Ile Pro
                100                 105                 110

Pro Glu Ile Gly Asn Leu Thr Asn Leu Val Tyr Leu Asp Leu Asn Asn
            115                 120                 125

Asn Gln Ile Ser Gly Thr Ile Pro Pro Gln Ile Gly Leu Leu Ala Lys
        130                 135                 140

Leu Gln Ile Ile Arg Ile Phe His Asn Gln Leu Asn Gly Phe Ile Pro
145                 150                 155                 160

Lys Glu Ile Gly Tyr Leu Arg Ser Leu Thr Lys Leu Ser Leu Gly Ile
                165                 170                 175

Asn Phe Leu Ser Gly Ser Ile Pro Ala Ser Val Gly Asn Leu Asn Asn
            180                 185                 190

Leu Ser Phe Leu Tyr Leu Tyr Asn Asn Gln Leu Ser Gly Ser Ile Pro
        195                 200                 205

Glu Glu Ile Ser Tyr Leu Arg Ser Leu Thr Glu Leu Asp Leu Ser Asp
    210                 215                 220

Asn Ala Leu Asn Gly Ser Ile Pro Ala Ser Leu Gly Asn Met Asn Asn
225                 230                 235                 240

Leu Ser Phe Leu Phe Leu Tyr Gly Asn Gln Leu Ser Gly Ser Ile Pro
                245                 250                 255

Glu Glu Ile Cys Tyr Leu Arg Ser Leu Thr Tyr Leu Asp Leu Ser Glu
            260                 265                 270

Asn Ala Leu Asn Gly Ser Ile Pro Ala Ser Leu Gly Asn Leu Asn Asn
        275                 280                 285

Leu Ser Phe Leu Phe Leu Tyr Gly Asn Gln Leu Ser Gly Ser Ile Pro
    290                 295                 300

Glu Glu Ile Gly Tyr Leu Arg Ser Leu Asn Val Leu Gly Leu Ser Glu
305                 310                 315                 320

Asn Ala Leu Asn Gly Ser Ile Pro Ala Ser Leu Gly Asn Leu Lys Asn
                325                 330                 335

Leu Ser Arg Leu Asn Leu Val Asn Asn Gln Leu Ser Gly Ser Ile Pro
            340                 345                 350

Ala Ser Leu Gly Asn Leu Asn Asn Leu Ser Met Leu Tyr Leu Tyr Asn
        355                 360                 365

Asn Gln Leu Ser Gly Ser Ile Pro Ala Ser Leu Gly Asn Leu Asn Asn
    370                 375                 380

Leu Ser Met Leu Tyr Leu Tyr Asn Asn Gln Leu Ser Gly Ser Ile Pro
385                 390                 395                 400

Ala Ser Leu Gly Asn Leu Asn Asn Leu Ser Arg Leu Tyr Leu Tyr Asn
                405                 410                 415

Asn Gln Leu Ser Gly Ser Ile Pro Glu Glu Ile Gly Tyr Leu Ser Ser
            420                 425                 430

Leu Thr Tyr Leu Asp Leu Ser Asn Asn Ser Ile Asn Gly Phe Ile Pro
        435                 440                 445

Ala Ser Phe Gly Asn Met Ser Asn Leu Ala Phe Leu Phe Leu Tyr Glu
    450                 455                 460
```

-continued

```
Asn Gln Leu Ala Ser Ser Val Pro Glu Glu Ile Gly Tyr Leu Arg Ser
465                 470                 475                 480

Leu Asn Val Leu Asp Leu Ser Glu Asn Ala Leu Asn Gly Ser Ile Pro
                485                 490                 495

Ala Ser Phe Gly Asn Leu Asn Asn Leu Ser Arg Leu Asn Leu Val Asn
            500                 505                 510

Asn Gln Leu Ser Gly Ser Ile Pro Glu Glu Ile Gly Tyr Leu Arg Ser
            515                 520                 525

Leu Asn Val Leu Asp Leu Ser Glu Asn Ala Leu Asn Gly Ser Ile Pro
        530                 535                 540

Ala Ser Phe Gly Asn Leu Asn Asn Leu Ser Arg Leu Asn Leu Val Asn
545                 550                 555                 560

Asn Gln Leu Ser Gly Ser Ile Pro Glu Glu Ile Gly Tyr Leu Arg Ser
                565                 570                 575

Leu Asn Asp Leu Gly Leu Ser Glu Asn Ala Leu Asn Gly Ser Ile Pro
            580                 585                 590

Ala Ser Leu Gly Asn Leu Asn Asn Leu Ser Met Leu Tyr Leu Tyr Asn
            595                 600                 605

Asn Gln Leu Ser Gly Ser Ile Pro Glu Glu Ile Gly Tyr Leu Ser Ser
            610                 615                 620

Leu Thr Tyr Leu Ser Leu Gly Asn Asn Ser Leu Asn Gly Leu Ile Pro
625                 630                 635                 640

Ala Ser Phe Gly Asn Met Arg Asn Leu Gln Ala Leu Ile Leu Asn Asp
                645                 650                 655

Asn Asn Leu Ile Gly Glu Ile Pro Ser Ser Val Cys Asn Leu Thr Ser
                660                 665                 670

Leu Glu Val Leu Tyr Met Pro Arg Asn Asn Leu Lys Gly Lys Val Pro
            675                 680                 685

Gln Cys Leu Gly Asn Ile Ser Asn Leu Gln Val Leu Ser Met Ser Ser
        690                 695                 700

Asn Ser Phe Ser Gly Glu Leu Pro Ser Ser Ile Ser Asn Leu Thr Ser
705                 710                 715                 720

Leu Gln Ile Leu Asp Phe Gly Arg Asn Asn Leu Glu Gly Ala Ile Pro
                725                 730                 735

Gln Cys Phe Gly Asn Ile Ser Ser Leu Glu Val Phe Asp Met Gln Asn
            740                 745                 750

Asn Lys Leu Ser Gly Thr Leu Pro Thr Asn Phe Ser Ile Gly Cys Ser
            755                 760                 765

Leu Ile Ser Leu Asn Leu His Gly Asn Glu Leu Glu Asp Glu Ile Pro
        770                 775                 780

Arg Ser Leu Asp Asn Cys Lys Lys Leu Gln Val Leu Asp Leu Gly Asp
785                 790                 795                 800

Asn Gln Leu Asn Asp Thr Phe Pro Met Trp Leu Gly Thr Leu Pro Glu
                805                 810                 815

Leu Arg Val Leu Arg Leu Thr Ser Asn Lys Leu His Gly Pro Ile Arg
            820                 825                 830

Ser Ser Arg Ala Glu Ile Met Phe Pro Asp Leu Arg Ile Ile Asp Leu
            835                 840                 845

Ser Arg Asn Ala Phe Ser Gln Asp Leu Pro Thr Ser Leu Phe Glu His
        850                 855                 860

Leu Lys Gly Met Arg Thr Val Asp Lys Thr Met Glu Glu Pro Ser Tyr
865                 870                 875                 880

Glu Ser Tyr Tyr Asp Asp Ser Val Val Val Thr Lys Gly Leu Glu
```

```
                    885                 890                 895
Leu Glu Ile Val Arg Ile Leu Ser Leu Tyr Thr Val Ile Asp Leu Ser
                900                 905                 910

Ser Asn Lys Phe Glu Gly His Ile Pro Ser Val Leu Gly Asp Leu Ile
            915                 920                 925

Ala Ile Arg Ile Leu Asn Val Ser His Asn Ala Leu Gln Gly Tyr Ile
        930                 935                 940

Pro Ser Ser Leu Gly Ser Leu Ser Ile Leu Glu Ser Leu Asp Leu Ser
945                 950                 955                 960

Phe Asn Gln Leu Ser Gly Glu Ile Pro Gln Gln Leu Ala Ser Leu Thr
                965                 970                 975

Phe Leu Glu Phe Leu Asn Leu Ser His Asn Tyr Leu Gln Gly Cys Ile
            980                 985                 990

Pro Gln Gly Pro Gln Phe Arg Thr Phe Glu Ser Asn Ser Tyr Glu Gly
        995                 1000                1005

Asn Asp Gly Leu Arg Gly Tyr Pro Val Ser Lys Gly Cys Gly Lys Asp
    1010                1015                1020

Pro Val Ser Glu Lys Asn Tyr Thr Val Ser Ala Leu Glu Asp Gln Glu
1025                1030                1035                1040

Ser Asn Ser Glu Phe Phe Asn Asp Phe Trp Lys Ala Ala Leu Met Gly
                1045                1050                1055

Tyr Gly Ser Gly Leu Cys Ile Gly Ile Ser Ile Ile Tyr Ile Leu Ile
            1060                1065                1070

Ser Thr Gly Asn Leu Arg Trp Leu Ala Arg Ile Ile Glu Glu Leu Glu
        1075                1080                1085

His Lys Ile Ile Met Gln Arg Arg Lys Lys Gln Arg Gly Gln Arg Asn
    1090                1095                1100

Tyr Arg Arg Arg Asn Asn Arg Phe
1105                1110

(2) INFORMATION FOR SEQ ID NO: 4:

(i) SEQUENCE CHARACTERISTICS:
        (A) LENGTH: 3573 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Tomato
        (B) STRAIN: Cf2

(xi) SEQUENCE DESCRIPTION: SEQ ID NO: 4:

GGTTTCTAGA AAAGTAGTCT CTTCACTTCA GTTTTTCACT CTTTTCTACC TCTTTACAGT    60

TGCATTTGCT TCGACTGAGG AGGCAACTGC CCTCTTGAAA TGGAAAGCAA CTTTCAAGAA   120

CCAGAATAAT TCCTTTTTGG CTTCATGGAT TCCAAGTTCT AATGCATGCA AGGACTGGTA   180

TGGAGTTGTA TGCTTTAATG GTAGGGTAAA CACGTTGAAT ATTACAAATG CTAGTGTCAT   240

TGGTACACTC TATGCTTTTC CATTTTCATC CCTCCCTTCT CTTGAAAATC TTGATCTTAG   300

CAAGAACAAT ATCTATGGTA CCATTCCACC TGAGATTGGT AATCTCACAA ATCTTGTCTA   360

TCTTGACTTG AACAACAATC AGATTTCAGG AACAATACCA CCACAAATCG GTTTACTAGC   420
```

-continued

| | |
|---|---|
| CAAGCTTCAG ATCATCCGCA TATTTCACAA TCAATTAAAT GGATTATTC CTAAAGAAAT | 480 |
| AGGTTACCTA AGGTCTCTTA CTAAGCTATC TTTGGGTATC AACTTTCTTA GTGGTTCCAT | 540 |
| TCCTGCTTCA GTGGGAATC TGAACAACTT GTCTTTTTTG TATCTTTACA ATAATCAGCT | 600 |
| TTCTGGCTCT ATTCCTGAAG AAATAAGTTA CCTAAGATCT CTTACTGAGC TAGATTTGAG | 660 |
| TGATAATGCT CTTAATGGCT CTATTCCTGC TTCATTGGGG AATATGAACA ACTTGTCTTT | 720 |
| TTTGTTTCTT TATGGAAATC AGCTTTCTGG CTCTATTCCT GAAGAAATAT GTTACCTAAG | 780 |
| ATCTCTTACT TACCTAGATT TGAGTGAGAA TGCTCTTAAT GGCTCTATTC CTGCTTCATT | 840 |
| GGGGAATTTG AACAACTTGT CTTTTTTGTT TCTTTATGGA AATCAGCTTT CTGGCTCTAT | 900 |
| TCCTGAAGAA ATAGGTTACC TAAGATCTCT TAATGTCCTA GGTTTGAGTG AGAATGCTCT | 960 |
| TAATGGCTCT ATTCCTGCTT CATTGGGGAA TCTGAAAAAC TTGTCTAGGT TGAATCTTGT | 1020 |
| TAATAATCAG CTTTCTGGCT CTATTCCTGC TTCATTGGGG AATCTGAACA ACTTGTCTAT | 1080 |
| GTTGTATCTT TACAATAACC AGCTTTCTGG CTCTATTCCT GCTTCATTGG GAATCTGAA | 1140 |
| CAACTTGTCT ATGTTGTATC TTTACAATAA TCAGCTTTCT GGCTCTATTC CTGCTTCATT | 1200 |
| GGGGAATCTG AACAACTTGT CTAGGTTGTA TCTCTACAAT AATCAGCTTT CTGGCTCTAT | 1260 |
| TCCTGAAGAA ATAGGTTACT TGAGTTCTCT TACTTATCTA GATTTGAGTA ATAACTCCAT | 1320 |
| TAATGGATTT ATTCCTGCTT CATTTGGCAA TATGAGCAAC TTGGCTTTTT TGTTTCTTTA | 1380 |
| TGAAAATCAG CTTGCTAGCT CTGTTCCTGA AGAAATAGGT TACCTAAGGT CTCTTAATGT | 1440 |
| CCTTGATTTG AGTGAGAATG CTCTTAATGG CTCTATTCCT GCTTCATTCG GAATTTGAA | 1500 |
| CAACTTGTCT AGGTTGAATC TTGTTAATAA TCAGCTTTCT GGCTCTATTC CTGAAGAAAT | 1560 |
| AGGTTACCTA AGGTCTCTTA ATGTCCTTGA TTTGAGTGAG AATGCTCTTA ATGGCTCTAT | 1620 |
| TCCTGCTTCA TTCGGGAATT TGAACAACTT GTCTAGGTTG AATCTTGTTA ATAATCAGCT | 1680 |
| TTCTGGCTCT ATTCCTGAAG AAATAGGTTA CCTAAGATCT CTTAATGACC TAGGTTTGAG | 1740 |
| TGAGAATGCT CTTAATGGCT CTATTCCTGC TTCATTGGGG AATCTGAACA ACTTGTCTAT | 1800 |
| GTTGTATCTT TACAATAATC AGCTTTCTGG CTCTATTCCT GAAGAAATAG GTTACTTGAG | 1860 |
| TTCTCTTACT TATCTATCTT TGGGTAATAA CTCTCTTAAT GGACTTATTC CTGCTTCATT | 1920 |
| TGGCAATATG AGAAATCTGC AAGCTCTGAT TCTCAATGAT AACAATCTCA TTGGGGAAAT | 1980 |
| TCCTTCATCT GTGTGCAATT TGACATCACT GGAAGTGTTG TATATGCCGA GAAACAATTT | 2040 |
| GAAGGGAAAA GTTCCGCAAT GTTTGGGTAA TATCAGTAAC CTTCAGGTTT TGTCGATGTC | 2100 |
| ATCTAATAGT TTCAGTGGAG AGCTCCCTTC ATCTATTTCC AATTTAACAT CACTACAAAT | 2160 |
| ACTTGATTTT GGCAGAAACA ATCTGGAGGG AGCAATACCA CAATGTTTTG GCAATATTAG | 2220 |
| TAGCCTCGAG GTTTTTGATA TGCAGAACAA CAAACTTTCT GGGACTCTTC AACAAATTT | 2280 |
| TAGCATTGGA TGTTCACTGA TAAGTCTCAA CTTGCATGGC AATGAACTAG AGGATGAAAT | 2340 |
| CCCTCGGTCT TTGGACAATT GCAAAAAGCT GCAAGTTCTT GATTTAGGAG ACAATCAACT | 2400 |
| CAACGACACA TTTCCCATGT GGTTGGGAAC TTTGCCAGAG CTGAGAGTTT AAGGTTGAC | 2460 |
| ATCGAATAAA TTGCATGGAC CTATAAGATC ATCAAGGGCT GAAATCATGT TCCTGATCT | 2520 |
| TCGAATCATA GATCTCTCTC GCAATGCATT CTCGCAAGAC TTACCAACGA GTCTATTTGA | 2580 |
| ACATTTGAAA GGGATGAGGA CAGTTGATAA ACAATGGAG GAACCAAGTT ATGAAAGCTA | 2640 |
| TTACGATGAC TCGGTGGTAG TTGTGACAAA GGGATTGGAG CTTGAAATTG TGAGAATTTT | 2700 |
| GTCTTTGTAC ACAGTTATCG ATCTTTCAAG CAACAAATTT GAAGGACATA TTCCTTCTGT | 2760 |
| CCTGGGAGAT CTCATTGCGA TCCGTATACT TAATGTATCT CATAATGCAT TGCAAGGCTA | 2820 |

-continued

```
TATACCATCA TCACTTGGAA GTTTATCTAT ACTGGAATCA CTAGACCTTT CGTTTAACCA   2880

ACTTTCAGGA GAGATACCAC AACAACTTGC TTCTCTTACG TTTCTTGAAT CTTAAATCT    2940

CTCCCACAAT TATCTCCAAG GATGCATCCC TCAAGGACCT CAATTCCGTA CCTTTGAGAG   3000

CAATTCATAT GAAGGTAATG ATGGATTACG TGGATATCCA GTTTCAAAAG GTTGTGGCAA   3060

AGATCCTGTG TCAGAGAAAA ACTATACAGT GTCTGCGCTA GAAGATCAAG AAAGCAATTC   3120

TGAATTTTTC AATGATTTTT GGAAAGCAGC TCTGATGGGC TATGGAAGTG GACTGTGTAT   3180

TGGCATATCC ATAATATATA TCTTGATCTC GACTGGAAAT CTAAGATGGC TTGCAAGAAT   3240

CATTGAAGAA CTGGAACACA AAATTATCAT GCAAAGGAGA AAGAAGCAGC GAGGTCAAAG   3300

AAATTACAGA AGAAGAAATA ATCGCTTCTA GACAAGTTAC CAATACCGAA AGATTTGATT   3360

TCAGAACTTC AGACTTTCAG GAGCCAAGAA TAAGAAGACG CTGGTGTAAA GGATTTGCTT   3420

CTTCCTGTGT TGCAGCTTAT GATGTTGGAT TAGATTTTTA GTTTTATAAG CTTTTCTTCA   3480

GTTGGGAAAA TGTAATATTA TGAATTTGAT GATATACAAT AAATGTTGTG TTTATTGAAA   3540

AAAAAAAAAA AAAAAAAAA AAAAAAAAA AAA                                  3573
```

(2) INFORMATION FOR SEQ ID NO: 5:

(i) SEQUENCE CHARACTERISTICS:
        (A) LENGTH: 301 amino acids
        (B) TYPE: amino acid
        (C) STRANDEDNESS: <Unknown>
        (D) TOPOLOGY: linear (ii) MOLECULE TYPE: peptide (iii) HYPOTHETICAL: YES (v) FRAGMENT TYPE: C-terminal (vi) ORIGINAL SOURCE:
        (A) ORGANISM: Tomato
        (B) STRAIN: Cf2

(xi) SEQUENCE DESCRIPTION: SEQ ID NO: 5:

```
Leu Gly Thr Leu Pro Glu Leu Arg Val Leu Arg Leu Thr Ser Asn Lys
1               5                   10                  15

Leu His Gly Pro Ile Arg Ser Ser Arg Ala Glu Ile Met Phe Pro Asp
            20                  25                  30

Leu Arg Ile Ile Asp Leu Ser Arg Asn Ala Phe Ser Gln Asp Leu Pro
        35                  40                  45

Thr Ser Leu Phe Glu His Leu Lys Gly Met Arg Thr Val Asp Lys Thr
    50                  55                  60

Met Glu Glu Pro Ser Tyr Glu Ser Tyr Tyr Asp Asp Ser Val Val Val
65                  70                  75                  80

Val Thr Lys Gly Leu Glu Leu Glu Ile Val Arg Ile Leu Ser Leu Tyr
                85                  90                  95

Thr Val Ile Asp Leu Ser Ser Asn Lys Phe Glu Gly His Ile Pro Ser
            100                 105                 110

Val Leu Gly Asp Leu Ile Ala Ile Arg Ile Leu Asn Val Ser His Asn
        115                 120                 125

Ala Leu Gln Gly Tyr Ile Pro Ser Ser Leu Gly Ser Leu Ser Ile Leu
    130                 135                 140

Glu Ser Leu Asp Leu Ser Phe Asn Gln Leu Ser Gly Glu Ile Pro Gln
145                 150                 155                 160

Gln Leu Ala Ser Leu Thr Phe Leu Glu Phe Leu Asn Leu Ser His Asn
```

```
                165                 170                 175
Leu Gln Gly Cys Ile Pro Gln Gly Pro Gln Phe Arg Thr Phe Glu Ser
                180                 185                 190

Asn Ser Tyr Glu Gly Asn Asp Gly Leu Arg Gly Tyr Pro Val Ser Lys
                195                 200                 205

Gly Cys Gly Lys Asp Pro Val Ser Glu Lys Asn Tyr Thr Val Ser Ala
                210                 215                 220

Leu Glu Asp Gln Glu Ser Asn Ser Glu Phe Phe Asn Asp Phe Trp Lys
225                 230                 235                 240

Ala Ala Leu Met Gly Tyr Gly Ser Gly Leu Cys Ile Gly Ile Ser Met
                245                 250                 255

Ile Tyr Ile Leu Ile Ser Thr Gly Asn Leu Arg Trp Leu Ala Arg Ile
                260                 265                 270

Ile Glu Lys Leu Glu His Lys Ile Ile Met Gln Arg Arg Lys Lys Gln
                275                 280                 285

Arg Gly Gln Arg Asn Tyr Arg Arg Asn Asn His Phe
                290                 295                 300

(2) INFORMATION FOR SEQ ID NO: 6:

(i) SEQUENCE CHARACTERISTICS:
        (A) LENGTH: 268 amino acids
        (B) TYPE: amino acid
        (C) STRANDEDNESS: <Unknown>
        (D) TOPOLOGY: linear (ii) MOLECULE TYPE: peptide (iii) HYPOTHETICAL: YES (v) FRAGMENT TYPE: C-terminal (vi) ORIGINAL SOURCE:
        (A) ORGANISM: Tomato
        (B) STRAIN: Cf9

(xi) SEQUENCE DESCRIPTION: SEQ ID NO: 6:

Thr Asn Leu Phe Met Gly Leu Gln Ile Leu Asp Leu Ser Ser Asn Gly
1               5                  10                  15

Phe Ser Gly Asn Leu Pro Glu Arg Ile Leu Gly Asn Leu Gln Thr Met
                20                  25                  30

Lys Glu Ile Asp Glu Ser Thr Gly Phe Pro Glu Tyr Ile Ser Asp Pro
                35                  40                  45

Tyr Asp Ile Tyr Tyr Asn Tyr Leu Thr Thr Ile Ser Thr Lys Gly Gln
50                  55                  60

Asp Tyr Asp Ser Val Arg Ile Leu Asp Ser Asn Met Ile Ile Asn Leu
65                  70                  75                  80

Ser Lys Asn Arg Phe Glu Gly His Ile Pro Ser Ile Ile Gly Asp Leu
                85                  90                  95

Val Gly Leu Arg Thr Leu Asn Leu Ser His Asn Val Leu Glu Gly His
                100                 105                 110

Ile Pro Ala Ser Phe Gln Asn Leu Ser Val Leu Glu Ser Leu Asp Leu
                115                 120                 125

Ser Ser Asn Lys Ile Ser Gly Glu Ile Pro Gln Gln Leu Ala Ser Leu
130                 135                 140

Thr Phe Leu Glu Val Leu Asn Leu Ser His Asn His Leu Val Gly Cys
145                 150                 155                 160

Ile Pro Lys Gly Lys Gln Phe Asp Ser Phe Gly Asn Thr Ser Tyr Gln
                165                 170                 175
```

```
Gly Asn Asp Gly Leu Arg Gly Phe Pro Leu Ser Lys Leu Cys Gly Gly
            180                 185                 190

Asp Asp Gln Val Thr Thr Pro Ala Glu Leu Asp Gln Glu Glu Glu Glu
            195                 200                 205

Glu Asp Ser Pro Met Ile Ser Trp Gln Gly Val Leu Val Gly Tyr Gly
            210                 215                 220

Cys Gly Leu Val Ile Gly Leu Ser Val Ile Tyr Ile Met Trp Ser Thr
225                 230                 235                 240

Gln Tyr Pro Ala Trp Phe Ser Arg Met Asp Leu Lys Leu Glu His Ile
            245                 250                 255

Ile Thr Thr Lys Met Lys Lys His Lys Lys Arg Tyr
            260                 265
```

(2) INFORMATION FOR SEQ ID NO: 7:

(i) SEQUENCE CHARACTERISTICS:
        (A) LENGTH: 66 amino acids
        (B) TYPE: amino acid
        (C) STRANDEDNESS: <Unknown>
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Tomato
        (B) STRAIN: Cf2

(xi) SEQUENCE DESCRIPTION: SEQ ID NO: 7:

```
Leu Asp Leu Ser Phe Asn Gln Leu Ser Gly Glu Ile Pro Gln Gln Leu
1               5                   10                  15

Ala Ser Leu Thr Phe Leu Glu Phe Leu Asn Leu Ser His Asn Tyr Leu
            20                  25                  30

Gln Gly Cys Ile Pro Gln Gly Pro Gln Phe Arg Thr Phe Glu Ser Asn
            35                  40                  45

Ser Tyr Glu Gly Asn Asp Gly Leu Arg Gly Tyr Pro Val Ser Lys Gly
            50                  55                  60

Cys Gly
65
```

(2) INFORMATION FOR SEQ ID NO: 8:

(i) SEQUENCE CHARACTERISTICS:
        (A) LENGTH: 65 amino acids
        (B) TYPE: amino acid
        (C) STRANDEDNESS: <Unknown>
        (D) TOPOLOGY: linear (ii) MOLECULE TYPE: peptide (v) FRAGMENT TYPE: internal (vi) ORIGINAL SOURCE:
        (A) ORGANISM: Tomato
        (B) STRAIN: Cf9

(xi) SEQUENCE DESCRIPTION: SEQ ID NO: 8:

```
Leu Asp Leu Ser Ser Asn Lys Ile Ser Gly Glu Ile Pro Gln Gln Leu
1               5                   10                  15

Ala Ser Leu Thr Phe Leu Glu Val Leu Asn Leu Ser His Asn His Leu
            20                  25                  30
```

```
Val Gly Cys Ile Pro Lys Gly Lys Gln Phe Asp Ser Phe Gly Asn Thr
        35                  40                  45
Ser Tyr Gln Gly Asn Asp Gly Leu Arg Gly Phe Pro Leu Ser Lys Leu
 50                  55                  60
Cys
65
```

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (iii) HYPOTHETICAL: YES (v) FRAGMENT TYPE: internal (xi) SEQUENCE DESCRIPTION: SEQ ID NO: 9:

```
Ser Gly Glu Ile Pro Gln Gln
 1               5
```

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (iii) HYPOTHETICAL: YES (v) FRAGMENT TYPE: internal (ix) FEATURE:
        (A) NAME/KEY: Region
        (B) LOCATION:2
        (D) OTHER INFORMATION:/product= "2"
            /note= "The second amino acid in this hypothetical
            peptide can be either Glutamic acid (E) as listed or
            Glutamine (Q)."

(xi) SEQUENCE DESCRIPTION: SEQ ID NO: 10:

```
Tyr Glu Gly Asn Asp Gly Leu Arg
 1               5
```

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: NO (xi) SEQUENCE DESCRIPTION: SEQ ID NO: 11:

```
TCNGGNGARA THCCNCARCA                                            20
```

-continued (2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(iii) HYPOTHETICAL: YES (iv) ANTI-SENSE: YES (xi) SEQUENCE DESCRIPTION: SEQ ID NO: 12:

CGNAGNCCRT CRTTNCCYTS RTA                23

(2) INFORMATION FOR SEQ ID NO: 13:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO: 13:

Phe Glu Gly His Ile Pro Ser
1           5

(2) INFORMATION FOR SEQ ID NO: 14:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 14:

Ser Gly Glu Ile Pro Gln Gln Leu Ala Ser Leu Thr Phe Leu Glu
1           5                 10               15

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

TAYSARGGNA AYGAYGGNCT NCG                23